United States Patent [19]
Lynn et al.

[11] 3,969,020
[45] July 13, 1976

[54] AUTOMATIC REFRACTION APPARATUS AND METHOD

[75] Inventors: John R. Lynn; George W. Tate, Jr., both of Dallas, Tex.

[73] Assignee: Giles C. Clegg, Jr., Dallas, Tex. ; a part interest

[22] Filed: Dec. 28, 1973

[21] Appl. No.: 429,143

[52] U.S. Cl. .................................. 351/17; 351/28; 351/29; 351/31
[51] Int. Cl.² .......................................... A61B 3/02
[58] Field of Search ................... 351/17, 28, 29, 39, 351/24

[56] References Cited
UNITED STATES PATENTS

| | | |
|---|---|---|
| 3,172,404 | 3/1965 | Copenhaver ...................... 351/24 X |
| 3,486,813 | 12/1969 | Johnston .............................. 351/17 |
| 3,602,580 | 8/1971 | Samuels ............................ 351/39 X |
| 3,718,386 | 2/1973 | Lynn et al. ........................... 351/23 |
| 3,822,932 | 7/1974 | Humphrey ........................... 351/17 |

Primary Examiner—Paul A. Sacher
Attorney, Agent, or Firm—Giles C. Clegg, Jr.

[57] ABSTRACT

Apparatus and method provide for automatically measuring the refractive error of the human eye and thus the prescription for lens or eye glasses for correcting this error. Test symbols are alternately presented at two different locations on a test screen under control of a programmed automatic data processing system. The symbols are viewed by a subject through a lens system whose power may be continuously varied also under control of the data processing system. The data processing system also varies the size of the symbols presented to compensate for the power of the lens system so that a given symbol will appear to the subject to be of constant size. In one illustrative embodiment of the present invention, the subject communicates with the data processing equipment via a subject response device to indicate his preference for one or the other of the symbols presented at the two locations. The data processing system interprets the responses to alter the presentation of symbols and elicit another response from the subject.

48 Claims, 17 Drawing Figures

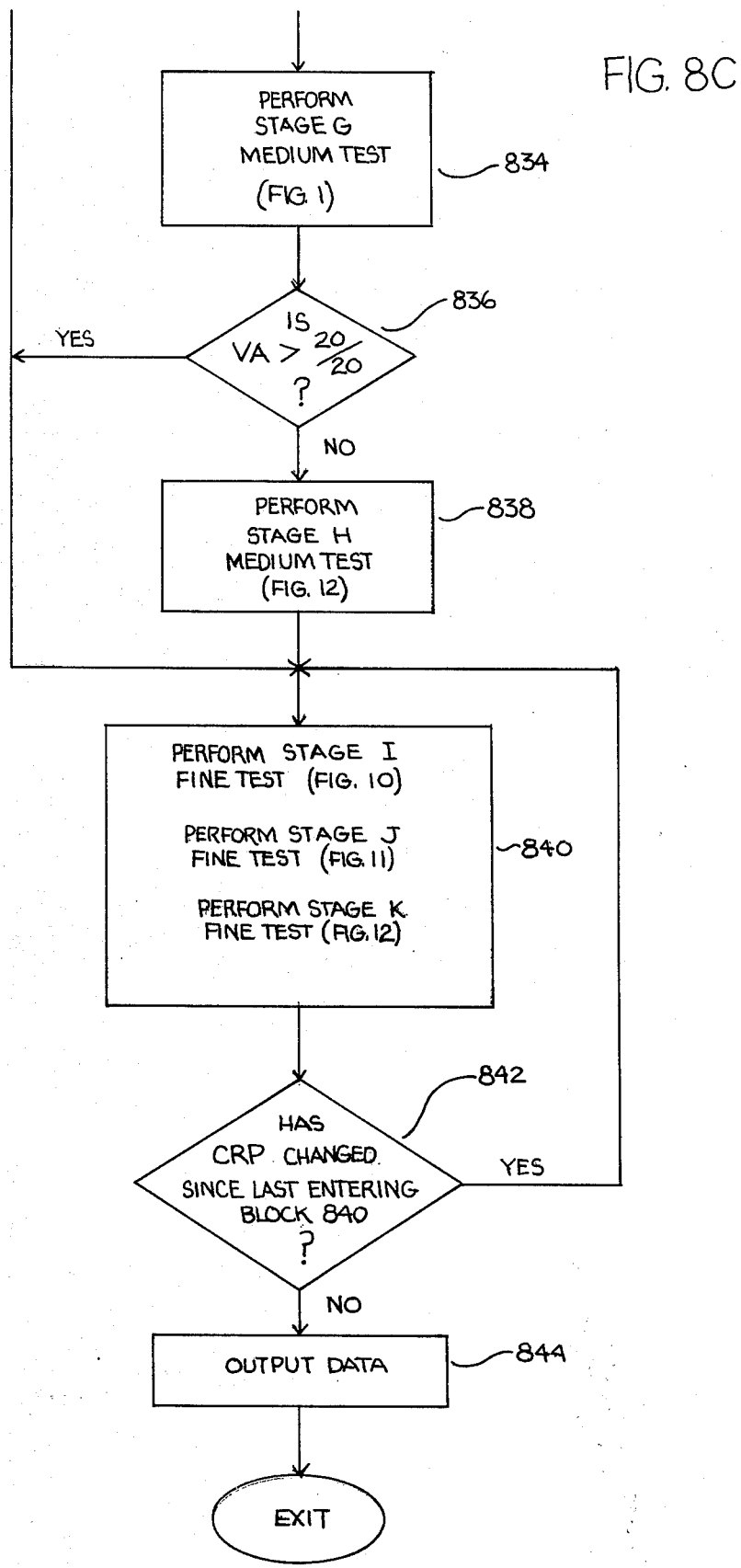

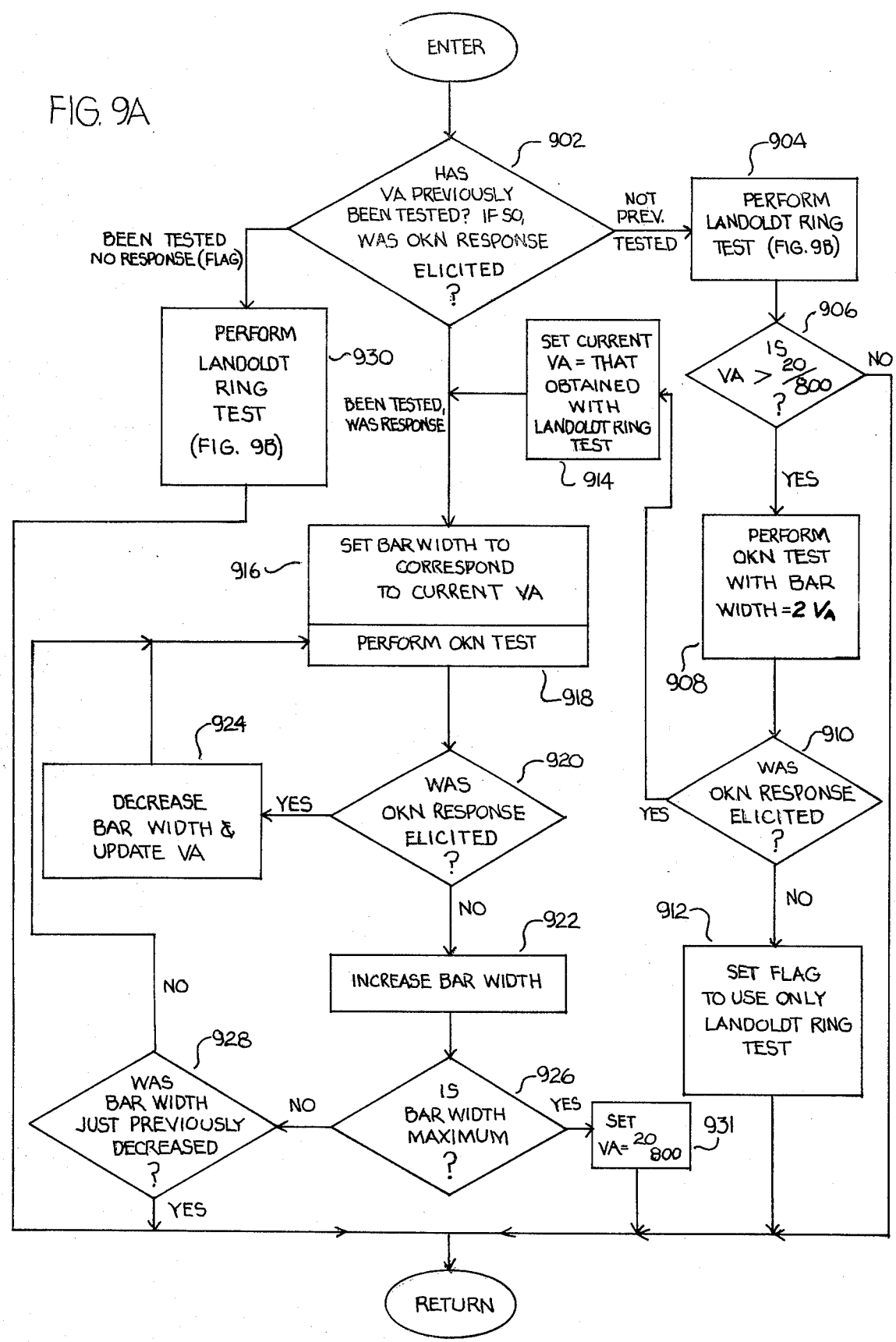

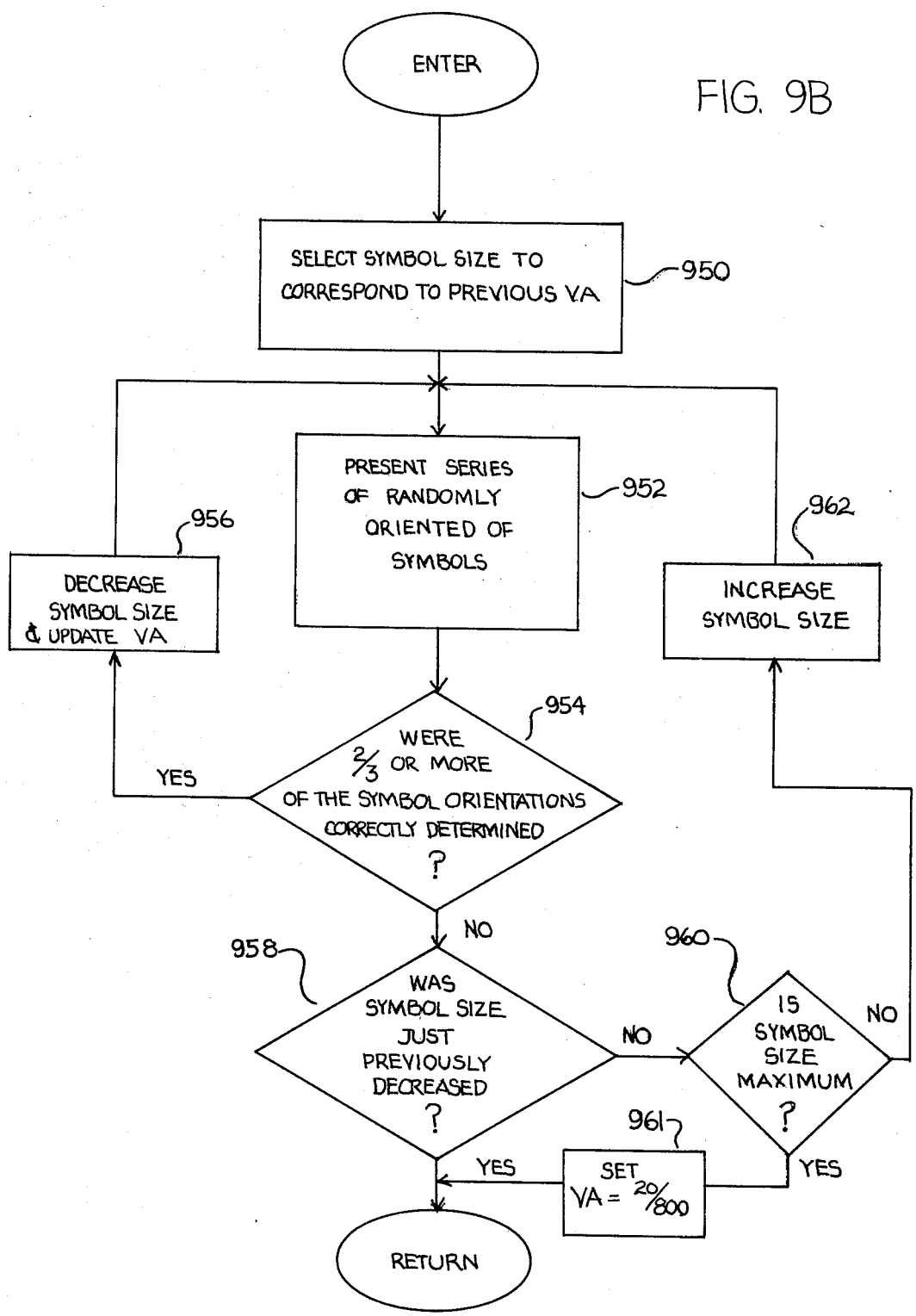

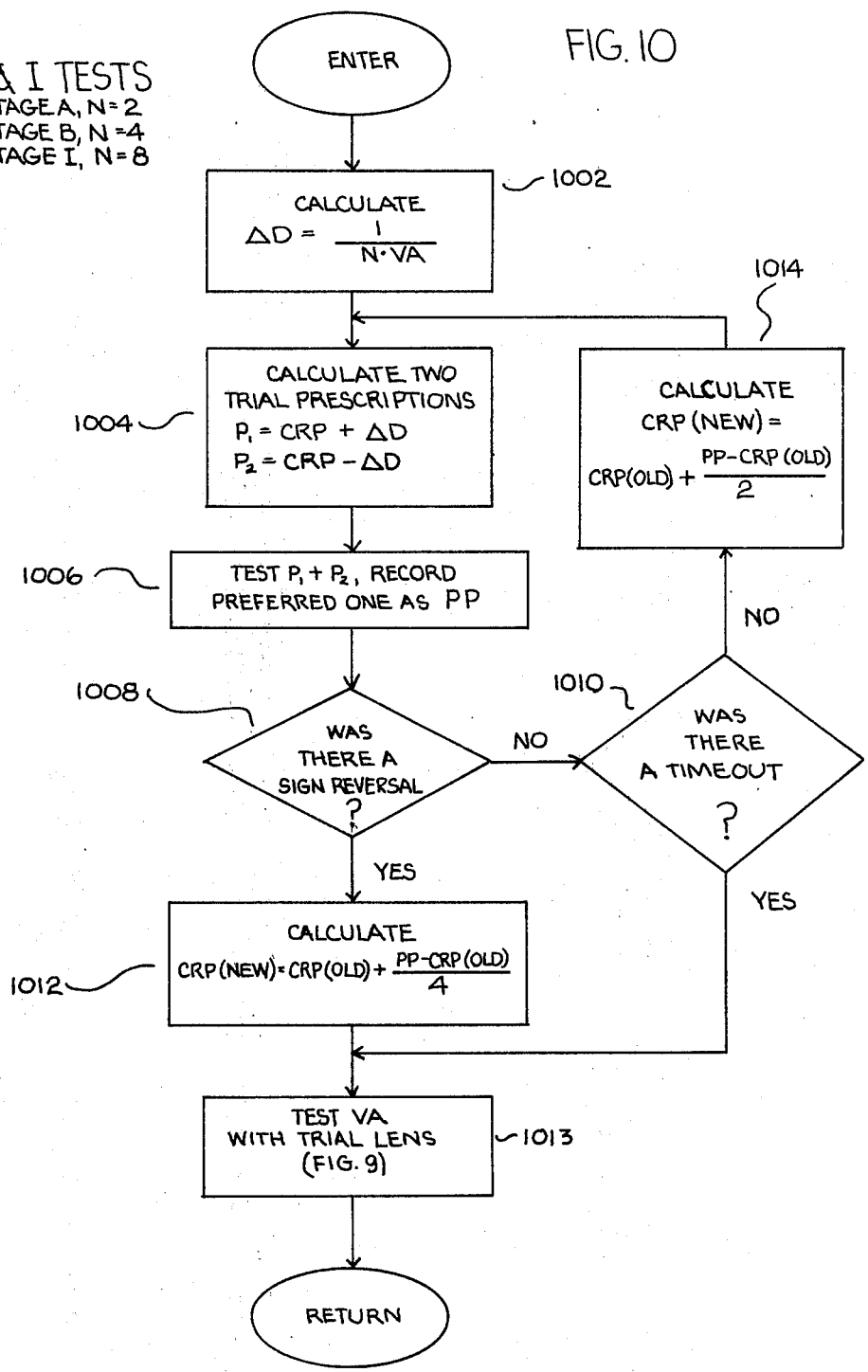

AUTOMATIC REFRACTION APPARATUS AND METHOD

BACKGROUND OF THE INVENTION

This invention relates to the field of human eye examination and more particularly to apparatus and method for automatically measuring refractive error in the vision of a human patient.

Light entering a human eye is refracted (bent) by the cornea and lens of the eye to converge and focus to some location behind the lens. If light from a distant object (theoretically at infinity) focuses on the retina of the eye then, if there is no distortion due to astigmatism (discussed momentarily), the eye is considered free from refractive error. When this is the case, the person can see distant objects clearly. In order to view a near object clearly, i.e., cause light from the object to converge and focus on the retina, it is necessary that the curvature of the lens of the eye be increased. This is achieved by the action of a muscle and is called "accommodation".

If light from a distant object converges to a point in front of the retina, the distant object is not seen clearly by the person and the person is said to be nearsighted. This "refractive error" of the eye can be corrected by an eye glass or lens which causes light from distant objects to diverge slightly as it passes through the lens. Such a lens is considered to have "negative refractive power." The light then passes through the lens of the eye and focuses on the retina thus enabling the person to clearly see the distant object.

If light from a distant object passes through the lens of the eye and converges toward a point behind the retina of the eye, then the person is said to be farsighted. Such a person may accommodate to place distant objects in focus, but near objects will not be seen sharply without additional accommodation. The farsighted condition may be corrected by placing an eyeglass or lens having "positive refractive power" between the eye and the object with such lens causing light from distant objects to converge as the light passes through the lens. The light then passes through the lens of the eye to focus on the retina so that distant objects can be viewed effectively, without accommodation.

Astigmatism was referred to earlier as causing a distortion of the focusing of light passing through the lens of the eye. Astigmatism is a condition in which the first refracting surface of the eye, i.e., the cornea, has unequal curvature which prevents the focusing of light to a common point on the retina. Correction of this condition is accomplished by means of an eyeglass or lens having cylindrical curvature. Cylindrical curvature is that curvature represented by the side of a cylinder (as opposed to spherical curvature which is that represented by the surface of a sphere). Cylindrical and spherical lenses may be either positive or negative, with positive lenses being ones which are thicker in the middle than at the edge and negative lenses being ones which are thinner in the middle than at the edge. Positive and negative refractive lenses were mentioned above when describing correction of refractive errors in the eye. By orienting a negative or minus cylindrical lens of appropriate power so that its long axis (the axis perpendicular to the direction of maximum curvature) is overlying and parallel with the positive astigmatic axis of the eye (that axis perpendicular to the direction of greatest curvature of the front surface of the eye), astigmatism may be corrected. The effect of such a cylindrical lens is to perform refraction of light in a direction perpendicular to the axis of astigmatism and by an amount sufficient to compensate for the difference in curvature of the surface of the eye.

Lens power is the ability of a lens to refract light, i.e., to converge light if the lens is positive or to diverge light if the lens is negative. Lens power is measured in diopters, which is the reciprocal of the focal length of the lens, measured in meters. The focal length of a lens is defined as the distance from the lens to a point (for spherical lens) or line (for cylindrical lens) at which light converges after the light enters the lens in parallel and passes therethrough (for a positive lens) or from which the light appears to diverge after entering the lens and passing therethrough (for a negative lens). These definitions are well-known in the field of optics and opthalmology.

At the present time, eye examinations to determine the prescription of eyeglasses to correct nearsightedness, farsightedness and astigmatism are performed manually by ophthalmologists, optometrists, and technician refractionists. These examinations generally begin with some type of rough screening to determine generally if the eye is nearsighted or farsighted. A number of objective measurements may be utilized for this rough screening including retinoscopy. In retinoscopy, the Examiner makes a rough determination of the refractive error of the subject's eye by positioning a so-called trial lens (one or a number of lenses having different corrective powers used for eye examinations), introducing a slit of light into the subject's eye, moving the slit of light at right angles to the length of the slit, and observing how it is reflected from the retina of the eye. The Examiner is able to determine generally the refractive error of the eye by the way the reflected light moves as the slit of light is moved and by changing the power of the trial lens until certain conditions of reflected movement are met.

Another kind of rough screening may be performed by alternately placing medium power plus and minus spherical lenses before the eye, superimposed with a trial lens, as the subject views a displayed object or symbol. The subject's indication of which medium power spherical lens provides the sharper viewing of the symbol guides the Examiner in changing the trial lens to solicit another choice from the subject. For example, if a plus power trial lens is being used and the subject indicates a preference for the combination of the trial lens and the plus spherical lens, then the Examiner changes the trial lens to be slightly more positive and again queries the subject as to which combination of the trial lens and the plus and minus spherical lens is preferred. An approximation of the power necessary to correct the subject's refractive error is indicated by a reversal in the subject's choice of the plus spherical lens combination over the minus spherical lens combination as he compares the two. It will be recognized that in this type of rough screening, the subject is usually choosing between two rather blurred images. For this reason, only a rough approximation of the correct power can be made.

If the previous eyeglass prescription is available either in written form or from the eyeglasses themselves, this information may be used in place of performing the rough screening. This is especially true if the subject can see fairly well with such eyeglasses since then, only a small adjustment may be necessary to correct the refractive error.

Further refinement of the rough screening results is necessary if the subject is to see clearly. This refinement may be either so-called "subjective refinement" requiring a conscious response by the subject as to his preference of, for example, displayed symbols, or objective refinement in which no conscious response is required of the subject. In either type of test, the purpose is to determine which corrective lenses will maximize the subject's visual acuity, that is, his ability to discriminate and identify the shapes of symbols of certain sizes displayed at a certain distance from the subject. Visual acuity is usually designated by fractions such as 20/20, 20/30, etc., in which the numerator represents the distance between the subject and the displayed symbols and the denominator represents a measure of the size of a symbol barely discernable by the subject. This size is in terms of the distance which a normal subject could see the symbol. For example, 20/40 means that the subject could barely read a symbol at 20 feet which a person with normal vision (20/20) could read at 40 feet.

One type of objective refinement involves the measurement of the electroencephalograms of a subject as he views test symbols with different trial lens configurations. These "visually evoked responses" (VER) may then be examined to determine the visual acuity of the subject as a function of the amplitudes of the signals recorded on the electroencephalograms. When the visual acuity is a maximum, the signal amplitude will be maximum.

Another type of objective examination for testing visual acuity is known as optokinetic nystagmus (OKN). In this test, the reflex "following movement" of the eye is monitored as black and white vertical bars are moved horizontally across a screen in front of an eye. The eye of a subject with good visual acuity will, by reflex action, fix upon one of the bars, follow it until it becomes difficult or impossible to see, and then jerk quickly back to assume fixation on another bar, with the following rate of the eye matching the rate of bar movement. The visual acuity is inversely proportional to the width of the bars required for the "following movement" to be elicited. Thus, a subject with poor vision requires larger bars than does a patient with good vision to exhibit the appropriate following movement of the eye.

Even if an accurate final prescription for eyeglasses can be determined by one of the objective refinement tests, the subject may be so accustomed to accommodating in order to see clearly that eyeglasses which eliminate the need for such accommodation are undesirable to the subject. Subjective refinement enables the Examiner to determine an eyeglass prescription which will provide the subject with maximum comfort. This may be desirable even if some sacrifice in sharpness of the visual image must be suffered. Thus, subjective refinement is generally desirable and this type of testing is the most difficult and time-consuming part of an eye examination. Much patience is required on the part of the Examiner and persistent attention to detail on the part of the subject. If the subject feels rushed or gets bored, a hasty and incorrect decision may lead the Examiner in the wrong direction in presenting test lenses to the subject. Backtracking may thus be required, but even if it isn't, rechecking is often desirable to ensure the accuracy of the examination.

It is an object of the present invention, in view of the above-described methods for manually measuring refractive error, to provide an automatic refraction apparatus and method implemented by automatic data processing equipment in combination with test symbol projection apparatus and a trail lens system.

It is another object of the present invention to provide automatic apparatus and method for subjectively determining the refractive error of a subject rapidly and accurately.

Presently-used trial lens systems consist of a pair of rotatable turrets, each holding lenses of different power about the periphery thereof. The different trial lenses in one turret may be rotated into position in front of one of the subject's eye while the lenses in the other turret may be rotated into position in front of the other eye of the subject. The subject views test symbols through the lenses in the turrets and expresses, for each eye, a preference for one lens of each of successively presented pairs of lenses. This is usually done by simply rotating one lens of a pair in front of an eye then rotating the other lens of the pair in front of the eye and asking the subject to express his preference. As is evident from the above description, the power of the lenses positioned in front of the eye is varied by discrete "jumps" with manual rotation of the turret. Thus, the accuracy of the determination of the refractive error is dependent, in part, on the magnitude of the lens power increments which can be presented to the subject.

It might be noted here that some turrets include two or even three coaxial, contiguous elements, each of which holds a plurality of lenses of different power. Each element is independently rotatable so that each lens of each element may be effectively aligned with each lens of the other elements. In this manner, the many different combinations of lenses provide a fairly large number of different trial lens powers which may be presented to the subject; however, the trial lens power changes must still be made in discrete jumps.

Another problem with the currently used turret systems is that the number of lenses through which the subject is to view the test symbol can vary depending upon the positioning of the turret elements. For example, for one setting three lenses may be positioned before the subject whereas for another setting, only one or two lenses may be aligned because one of the turret elements is positioned so that only an opening (with no lens) in the element is aligned with the other lens or lenses. Of course, with variations of the number of lenses through which a test symbol is viewed, light transmission through the lens combinations varies and thus the relative brightness of the symbol varies. This may adversely influence the preferences expressed by the subject in choosing between the test symbols.

It is still another object of the present invention to provide automatic refraction apparatus and method having a continuously variable lens system through which the subject views a test symbol.

It is also an object of the present invention to provide apparatus and method for automatically controlling the variation in power of the lens system.

It is a further object of the present invention to provide method and apparatus in which periodic objective visual acuity tests are utilized as one determinant of the choice of lens system power to present to the subject.

It is still a further object of the present invention to provide such a lens system in which the number of lenses before an eye is maintained constant as the power of the lens system is varied.

If a test symbol of fixed size is presented on a screen for viewing by a subject, and the power of the lens system is varied, it will appear to the subject that the size of the symbol varies. Thus, when the subject is called upon to indicate a preference based on sharpness or clearness, between the test symbol viewed through the lens system of one power and the test symbol viewed through the lens system of a different power, the subject may be influenced by the size of the symbol. This is undesirable and even though the subject is cautioned against this, his preferences may still be influenced by the size of the symbol.

It is therefore an object of one aspect of the present invention to provide refraction apparatus and method for automatically varying the size of a test symbol presented for viewing by a subject to compensate for changes in power of the lens system through which the subject is viewing the symbol.

It is also an object of this aspect of the present invention to automatically control the magnification of test symbols so that they appear to be of constant size to a subject regardless of the variation in power of the lens system through which the subject is viewing the symbol.

As discussed above, in the course of an eye examination to determine refractive error using presently known techniques, a subject is called upon to indicate a preference between a test symbol viewed through one set of trial lens and the same test symbol viewed through a different set of trial lens. Preferences are solicited for successive pairs of lens combinations compared with the test symbol being presented at the same location on a screen. The examiner successively presents the trial lens of each pair to the subject and the subject then indicates a preference either for the "previous" symbol or the "present" symbol (or something similar to this). Because the subject must indicate a preference between what appears to be consecutively presented symbols at the same location on the test screen, confusion can arise in the course of the subject attempting to communicate his preferences to the examiner.

It is an object of another aspect of the present invention to provide apparatus and method for presenting test symbols alternately at two different locations for viewing by a subject to thereby enable the subject to indicate a preference by identifying the location of the "preferred" symbol.

It is an object of still another aspect of the present invention to provide apparatus and method for presenting test symbols simultaneously at two different locations for viewing by a subject.

It is also an object of the present invention to provide a manual response device by which a subject can identify at which of two locations a preferred test symbol is being presented.

It is still another object of the present invention to automatically monitor the direction of gaze of the subject and to change the lens power of the lens system when the direction of gaze changes from the first location to the second location.

SUMMARY OF THE INVENTION

The above and other objects and advantages of the present invention are realized in apparatus and method for subjectively determining the refractive error of a subject under control of a programmable automatic data processing system. In one embodiment of the invention a test symbol is presented on a test screen alternately at two different locations. The subject views the test symbol through a continuously variable lens system controlled by automatic data processing equipment. The lens system is controlled to provide one power setting for the symbol presented at one location on the screen and a different power setting for the symbol presented at the other location. The subject indicates a preference for the symbol at one of the two locations based on sharpness and visual clarity of the symbol by operating a manual response device identifying the location. The subject's response is then used by the data processing equipment to automatically control the power settings of the lens systems for subsequently presented test symbols.

Periodic, and preferably frequent, visual acuity test are made and the acuity test results used by the data processing equipment in conjunction with the patient responses to control the power settings of the lens system.

In accordance with one aspect of the invention, the size of the test symbols is controlled by the data processing equipment in conjunction with the control of the power setting of the lens system so that the two test symbols presented at the two locations will appear to the subject to be the same size regardless of the variation in power of the lens system.

In accordance with another aspect of the invention, a direction of gaze monitor is employed to signal the data processing equipment when the subject changes his direction of gaze from one location where the test symbol is presented to the other location, and vice versa. In response to such a signal, the data processing equipment automatically causes a change in the power setting of the lens system.

BRIEF DESCRIPTION OF THE DRAWINGS

The present invention, both as to its organization and manner of operation, together with further objects and advantages thereof may be best understood by way of illustration and example, when taken in conjunction with the accompanying drawings, in which:

FIGS. 8A, 8B and 8C are a flow chart of one illustrative process or program for utilizing the apparatus of FIGS. 1 and 5 to perform refractive error tests;

FIGS. 9A and 9B are flow charts of a subprogram of the FIG. 8 program for testing visual acuity; and FIGS. 10, 11A, 11B, 12A and 12B are flow charts of subprograms of the program of FIG. 8.

DESCRIPTION OF THE PREFERRED EMBODIMENT

Figure 1:
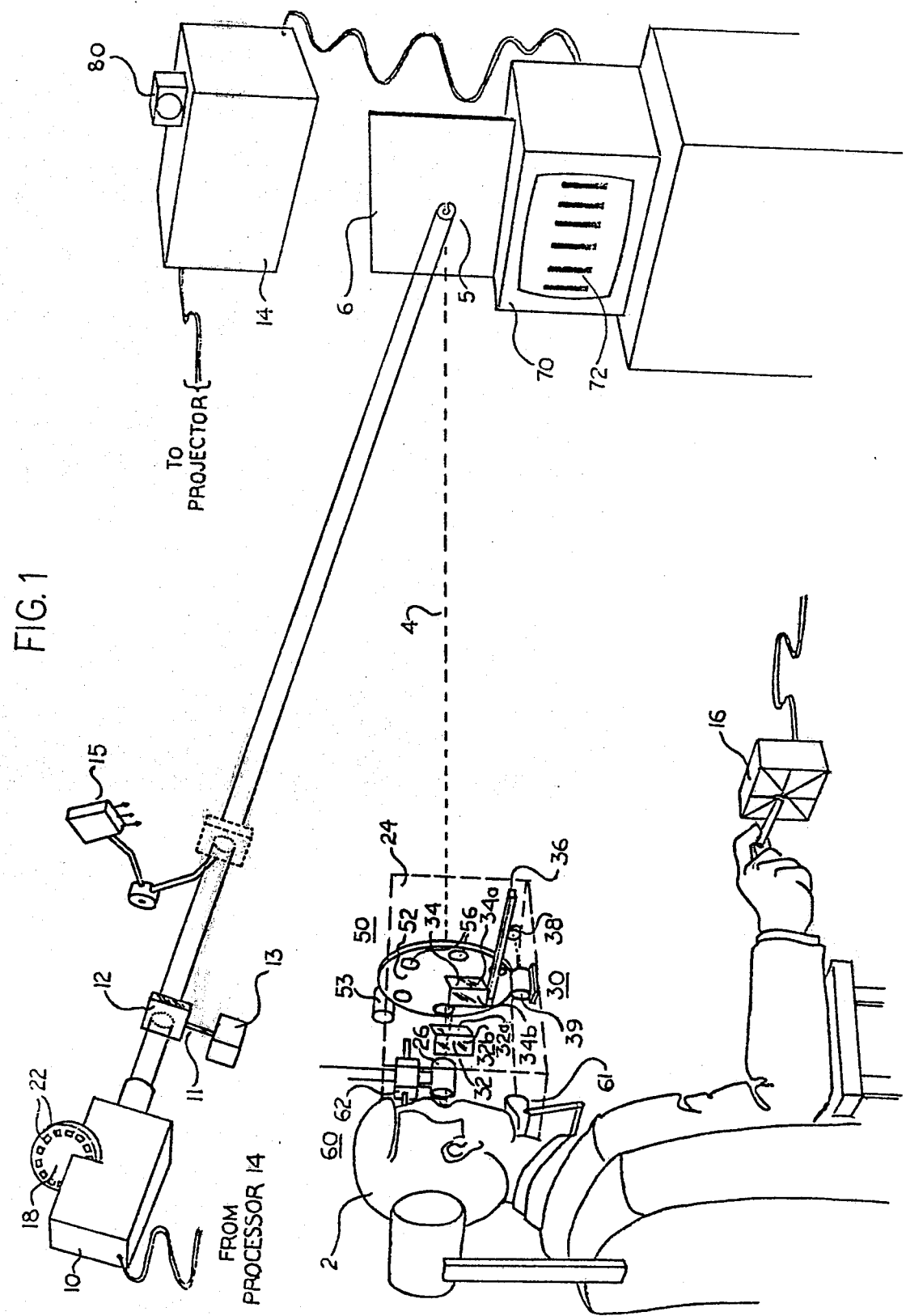
FIG. 1 is a perspective view illustrating the general arrangement of the various elements of one illustrative embodiment of the invention.

Referring to FIG. 1, there is shown illustrative apparatus for automatically, subjectively measuring refractive error of the eyes of a subject 2. Test symbols and other visual stimuli are presented to the subject under control of a programmed automatic data processor or computer 14. The subject views the test symbols through a trial lens system, also controlled by the processor 14 and communicates responses to the processor. The subject is automatically given instructions as the examination proceeds so that no human intervention is necessary once the examination is underway.

The subject 2 is positioned a predetermined distance from a test screen 6 on which test letters or symbols are displayed for viewing by the subject. A projector 10 operates under control of the processor 14 to project test symbols on the screen 6. The test symbols used might be any of the standard symbols used in performing eye examinations. For example, the symbol 5 shown on the screen 6 is the so-called Landoldt ring. This symbol consists of a ring with an opening or break in one of eight locations about the ring — either in the upper part of the ring, the upper right hand part, the right hand part, etc. The Landoldt ring symbol is commonly used in performing subjective visual acuity tests. The symbol is displayed and then the subject is asked to indicate where the opening or break in the ring is located. The accuracy of the responses of the subject to the presentation of different size Landoldt rings provides a measure of the subject's visual acuity.

The use of the Landoldt ring symbol is especially advantageous in the present invention since a relatively simple manual response device 16 may be used to enable the subject 2 to communicate his responses to the processor 14. The manual response device 16 is situated within convenient reach of subject 2 so that during the course of the eye examination, the subject may operate the response device 16 with his hand. The use of the manual response device 16 will be discussed in greater detail later.

The projector 10 includes a rotatable wheel 18 which holds a plurality of transparencies or slides 22 containing different size symbol images. The processor 14 signals the projector 10 to cause it to rotate the wheel 18 to display symbols of selected size on the screen 6. As will be discussed later in conjunction with FIG. 3, the projector 10 also includes apparatus for rotating the projected symbols so that the break in the ring may be positioned in any one of the above-defined eight locations. Rotation and positioning of the symbols is also carried out under control of the processor 14.

The subject 2 views the test symbols presented on the screen 6 through a trial lens system included in a trial lens system housing 24 supported by a suitable floor or wall support (not shown). The trial lens system includes a lens housing 26 positioned immediately in front of the subject's right eye, a variable mirror assembly 30 positioned in front of the lens housing 26, and a turret 52 positioned between the mirror assembly 30 and the screen 6. (Although not shown in the drawing, the trial lens system includes a second lens housing, mirror assembly, and turret which are positioned in front of the left eye of the subject during the examination). The lens housing 26 contains a primary spherical lens and a pair of so-called variable crossed cylinders used in determining astigmatic error. Variable crossed cylinders consist of two cylindrical lenses of equal power but opposite sign, i.e., one is a plus cylinder and the other is a minus cylinder. The cylinders are positioned one in front of the other in the housing 26 and in the pathway 4 of the direction of gaze of the subject so that the axes of the cylinders are perpendicular to the direction of gaze. The cylinders are rotatable with respect to each other so that the angle between the axes thereof may be varied — it is for this reason that the cylinders are known as variable cross cylinders. Because the powers of the two cylinders are equal but opposite in sign, when the axes of the cylinders are aligned (parallel) the cylinders cancel each other so that the power of the combination is zero; when the axes are 90° apart, the combination has a maximum positive cylindrical power along the plus cylinder axis and a maximum negative cylindrical power along the minus cylinder axis. As is well known in the refractive art, by varying the angle between the axes of the crossed cylinders from 0° to 90°, the location of the plus and minus axes of the variable crossed cylinder system (which are always 90° from one another in any cylindrical lens or lens system) and the cylindrical power of the system vary in a predictable manner. Specifically, the plus axis of the combined system is located exactly 45° from a line bisecting the axes of the individual plus and minus cylinders in a direction toward the axis of the plus cylinder. As already indicated, the location of the minus axis of the combined system is 90° from the plus axis of the system. The cylindrical power along the plus axis of the variable crossed cylinder combination varies from zero to a positive maximum and the cylindrical power along the minus axis of the combination varies from zero to a negative maximum.

With proper rotational positioning of the variable crossed cylinders, the power and axis necessary to correct astigmatic error can be determined. One such test for determining the axis of astigmatism will be described later when discussing an exemplary method of utilizing the FIG. 1 apparatus.

Figure 2:
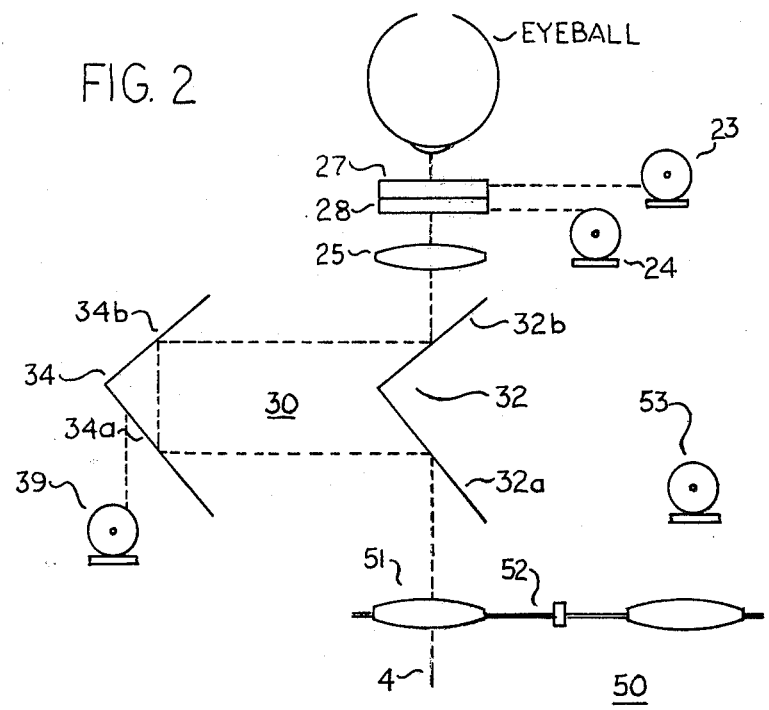
FIG. 2 is a diagrammatic showing of the trial lens system of FIG. 1.

The variable crossed cylinders and primary spherical lens of the lens housing 26 are shown in FIG. 2 which provides a top diagrammatic view of the lens system of FIG. 1. The two cylinders are indicated at 27 and 28 rotatably driven by servo motors 23 and 24 respectively. The motors 23 and 24 operate under control of the processor 14 (the motors 23 and 24 are not shown in FIG. 1).

The primary spherical lens (shown at 25 in FIG. 2) included in the lens housing 26 (FIG. 1) is used in conjunction with the mirror assembly 30 and the turret 52 for presenting before the subject 2 lens combinations having continuously variable spherical power. The spherical power of the lens system is variable in a continuous, as opposed to a discrete, fashion by reason of the novel mirror assembly 30. The power of the lens system is varied by the mirror assembly in the same manner that the power of a telescope is varied. Recall that in a telescope, a number of lenses are coaxially positioned and that the power of the telescope is varied simply by varying the distance between the lenses. For the trial lens system of FIGS. 1 and 2, the effective distance (distance traveled by the light waves) between the primary lens 25 in the lens housing 26 and the lens in the turret assembly 50 is varied by adjustment of the mirror assembly 30 with no movement of either the primary lens or the lens in the turret assembly 50 being required.

The mirror assembly 30 includes a fixed pair of mirrors 32 positioned at right angles to each other and a movable pair of mirrors 34 also positioned at right angles to each other (see FIGS. 1 and 2). The fixed pair 32 is positioned in the pathway 4 of the direction of gaze of the subject. One mirror 32a of the pair 32 is positioned to reflect laterally to the right of the subject 2 light traveling along the pathway 4 from the symbols displayed on the screen 6. The mirror pair 34 is positioned laterally of the mirror pair 32 so that a first mirror 34a of the pair 34 is in the pathway of the light reflected from the mirror 32a. The plane of the mirror 34a is parallel to the plane of the mirror 32a and thus, of course, the plane of the other mirror 34b of the pair 34 is parallel to the plane of the other mirror 32b of the pair 32. With this configuration, the light reflected from the mirror 32a to the mirror 34a will, in turn, be reflected to the mirror 34b and then to the mirror 32b as indicated in FIGS. 1 and 2. The light is then reflected through the lenses in lens housing 26 to the eye of the subject 2.

By moving the mirror pair 34 toward or away from the mirror pair 32 along a line bisecting the angles formed by each mirror pair, the effective distance between the primary spherical lens 25 and the lens (indicated by numeral 51 in FIG. 2 of the turret assembly 50 is varied. To facilitate such movement, the mirror pair 34 is mounted on a bar 36 (FIG. 1) which, together with a motor driven wheel 38, forms a conventional rack and pinion gear. Rotation of the wheel 38 causes the mirror pair 34 to move toward or away from the mirror pair 32 depending upon the direction of rotation of the wheel. The wheel 38 is driven by a servo motor 39 under control of the processor 14.

Provision of the mirror assembly 30 to vary the power of the trial lens system is desirable since it eliminates the need to move any of the lenses and therefore avoids alignment problems which might otherwise arise if movement of the lenses were required. Proper alignment of the lenses in a trial lens system is necessary to prevent distortion of the image or symbols viewed by the subject. With the mirror assembly 30, some misalignment of the mirrors, i.e., some movement of the mirrors laterally (with respect to the pathway of the light from the test symbol) is tolerable since this will not introduce distortion. On the other hand, movement of a lens laterally (with respect to the light pathway) introduces distortion. Of course, a telescope-type trial lens system could be utilized with the FIG. 1 apparatus to provide the desired continuous variation of lens power. It is apparent that the distance between the lenses in such an arrangement could be controlled by the processor 14 in a manner similar to that by which the mirror assembly 30 is controlled. Also, the mirror pairs 32 and 34 could be replaced by reflecting right angle prisms.

The turret 52 of the trial lens system of FIG. 1 includes a plurality of spherical lenses 56 of different power spaced about the periphery thereof. The turrets 52 is rotatable by a servo motor 53 to enable selective positioning of a different one of the lenses 56 in front of the eye of the subject 2. As with the other equipment of FIG. 1, the motor 53 operates under control of the processor 14.

The combination of the turret 52, mirror assembly 30 and primary lens 25 in the housing 26 enables presenting to the subject 2 a wide and continuous range of spherical powers. For example, a lens in the turret 52 having a fairly small power (+1 diopter) could be positioned for viewing therethrough by the subject 2 and then the mirror pair 34 moved to gradually increase the total power of the lens system. If the mirror pair 34 were moved to its limit and still a greater lens power were desired, then a lens in turret 52 having greater power would be rotated into place and the mirror pair 34 repositioned and moved to again cause a further gradual increase in the total power of the lens system. This process could be continued to provide a gradual and continuous increase in the power of the trial lens system until the lens in turret 52 having the greatest spherical power were positioned before the subject and the mirror pair 34 were moved to its limit in the direction of increasing the lens system power.

The lens housing 26 is attached to vertex distance measuring apparatus 60. As fully described in copending patent application filed by George W. Tate. Jr., Ser. No. 429,020, now U.S. Pat. No. 3,904,280, the vertex distance measuring apparatus 60 provides for determining the so-called vertex distance — the distance between the cornea of the subject's eye and the surface of the lens nearest the subject (in this case the variable crossed cylinder 27 of FIG. 2). Since the power of a trial lens system needed to correct refractive error depends in part upon the vertex distance, it is important to either maintain the vertex distance constant throughout an eye examination or to take into account in conducting the examination any vertex distance changes which occur during the examination. As fully described in the aforementioned copending application, the apparatus 60 may be used either in maintaining a constant vertex distance or in detecting any changes in the vertex distance.

The apparatus 60 includes a housing 62 and a feeler bar 64 slidable in the housing. The feeler bar 64 contacts the forehead of the subject 2 to either detect movement of the subject's forehead toward or away from the apparatus or to prevent movement of the subject's head. In the latter case, after the apparatus has been used to measure the vertex distance, the feeler bar 64 is locked in place against the subject's forehead so that movement of the subject's forehead toward the apparatus 60 is prevented. (A chin rest 61 is also provided to stabilize the vertex distance). In the former case, any movement of the forehead of the subject 2 causes a corresponding movement of the feeler bar 64 within the housing 62 and this movement causes the generation of a signal which is transmitted to the processor 14. The polarity and magnitude of the signal indicate the direction of movement of the subject and the magnitude of such movement respectively. In response to the signal, the processor 14 automatically causes appropriate adjustment in the trial lens system, and in particular in the mirror assembly 30 to compensate for the change in the vertex distance.

As described earlier, visual acuity may be measured by presenting Landoldt ring symbols to the subject and then eliciting from the subject a response as to the location of the break or opening in the rings. As also discussed earlier, the projector 10 rotates and positions the projected Landoldt ring symbols under control of the processor 14. The projector 10 and the apparatus for causing rotation of the symbols, is shown in detail in FIG. 3. As there shown, the projector includes a standard concave mirror 302, condenser lenses 310 positioned in front of the mirrors and a projection lamp 306 positioned between the mirror 302 and the lenses 310. The wheel 18 containing the transparencies of the different size symbol images is positioned to rotate in front of the lenses 310. The wheel 18 is rotated by a friction wheel 314 which engages the perimeter of the wheel 18 and is driven by a servo motor 318. The processor 14 of FIG. 1 controls the servo motor 318 to cause the rotation and proper positioning of the wheel 18. A focusing lens 322 is positioned in front of the wheel 18 and aligned with the condenser lenses 310 and the lamp 306. A so-called dove prism 326 is positioned in front of the lens 322 and aligned therewith. When a dove prism is rotated, any image being projected through the prism in the direction of the axis of rotation is also rotated. The dove prism 326 of FIG. 4 is encircled by a collar 328 the perimeter of which is engaged by a wheel 330 driven by a servo motor 332. The servo motor 332 is controlled by the processor 14 of FIG. 1 to rotate the wheel 330 and thereby cause a rotation of the collar 328 and dove prism 326 to position the prism at any desired angular position.

Figure 3:
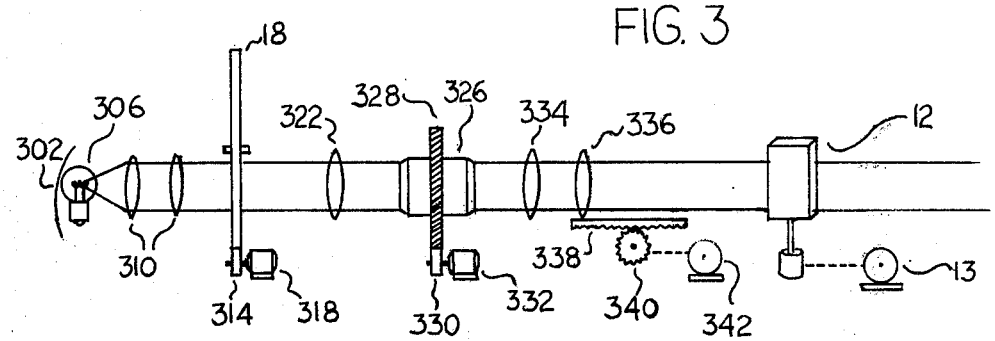
FIG. 3 shows one illustrative embodiment of the symbol projection apparatus of FIG. 1.
Figure 4:
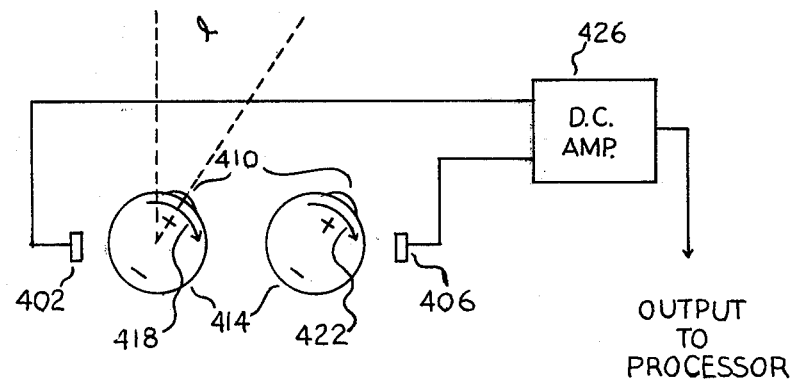
FIG. 4 is a diagrammatic showing of an electrooculograph monitor.

The projector of FIG. 3 also includes a pair of lenses 334 and 336 for varying the size of the symbol projected onto the screen 6 of FIG. 1. Lens 334 is aligned with the other lenses of the projector in fixed position and lens 336 is moveable with respect to lens 334. Lens 336 is mounted on a rack 338 of a rack and pinion gear. The pinion 340 is driven by a servo motor 342 under control of the processor 14 of FIG. 1. Of course, by moving the lens 336 either toward or away from the fixed lens 334, the size of the projected symbol is varied. This capability of varying the size of the projected symbol is provided to compensate for variation in the power of the lens system. That is, when a test symbol (which could be but need not be the Landoldt ring symbol) of fixed size is to be presented on the screen and the subject is to view the symbol through the lens system set alternately at two different powers, it is desirable that the apparent size of the symbol remain constant to the subject so that when called upon to indicate a preference between the two power settings, he will not be influenced by any apparent change in the size of symbol. Thus, when the processor 14 of FIG. 1 causes the lens system to change from one power to another for purposes of eliciting a preference, the processor also causes an adjustment of the position of lens 336 of FIG. 3 to either increase or reduce the size of the projected symbol by an amount appropriate to compensate for any apparent change in size caused by the change of the lens system power.

In order to reduce confusion in eliciting preferences from the subject, the FIG. 1 system includes a prism 12 positioned in the pathway of the projected symbol and rotatable about a vertical axis between two positions for causing the projected symbols to appear at either of two horizontally spaced locations on the screen 6. When the subject 2 is requested to indicate a preference for one of two power settings of the lens system, the symbol is projected at one location for one of the power settings and the other location for the other power setting. The subject 2 then need only indicate the location of the "preferred" symbol, i.e., indicate the left-most location or the right-most location.

The prism 12 is mounted on a vertical shaft 11 which, in turn, is rotatably driven by a servo motor 13 under control of the processor 14. When the processor 14 changes the lens system power setting in the course of the eliciting responses from the subject, it also signals the servo motor 13 to rotate the shaft 11 and thus the prism 12 to cause the projected symbol to move between the two locations on the screen. The locations on the screen at which the symbol appears are spaced reasonably close together (e.g. 6 inches) so that the symbol when presented in either location is well within the field of view of the subject looking through the lens system.

Rather than program the processor 14 to automatically change the location of the projected symbol and the power setting of the lens system so that the subject 2 must involuntarily change his direction of gaze to enable him to view the symbol, it may be desirable to allow the subject to alternately view two spaced, simultaneously presented symbols at his choosing, and to automatically change the power setting of the trial lens when the subject's direction of gaze changes. A simple beam splitting prism 15 could be positioned in the symbol image pathway to cause the image to be projected simultaneously at the two locations on the screen 6. The direction of gaze of the subject is then monitored so that when his gaze moves from one of the locations on the screen toward the other location, the processor 14 automatically causes the trial lens system to change power settings. Similarly, when the gaze of the subject moves back toward the first mentioned location, the processor 14 automatically returns the power setting of the trial lens system to the first mentioned setting.

A number of arrangements may be provided for monitoring a subject's direction of gaze including a device known as an electro-oculograph monitor diagrammatically illustrated in FIG. 4. The technique of electro-oculography is based on the fact that a D.C. potential difference exists between the corneal surface (at the front of the eye) and the posterior vascular layer of the eyeball. This potential is known as the corneal-retinal standing potential and is illustrated in a schematic manner in FIG. 6 which shown the corneal portion 410 of the eyeball having a positive potential with respect to the posterior or retinal portion 414. This standing potential varies from person to person somewhat but has been observed to be as great as 1 millivolt in some individuals and as small as 0.30 millivolts in others. Electrodes 402 and 406, situated as shown in FIG. 4, can be used to monitor eye movements in a horizontal plane by measuring variations in the electric field surrounding the eye produced by the corneal-retinal standing potential. For example, suppose that the eyeballs illustrated schematically in FIG. 4 rotate in a horizontal plane in the direction indicated by arrows 418 and 422 through the angle $\alpha$. This would bring the positive corneal surfaces of the eyes closer to electrode 406 and similarly bring the negative posterior regions closer to electrode 402. This would increase the potential difference between the two electrodes from its initial value before the eye movement. The algebraic sign of the movement is also indicated by the direction of the potential difference change as measured at the electrodes. A more complete discussion of the voltage produced by eye movement is found in copending patent application, Ser. No. 335,572, now U.S. Pat. No. 3,883,235, filed Feb. 26, 1973. A D.C. amplifier 426 is used to amplify the relatively small voltage difference produced with eye movement and the resultant output is supplied to the processor 14. This output will be either positive or negative depending upon the direction of the eye movement.

The electrodes 402 and 406 used to measure the eye position could be placed on some type of face mask worn by the subject or alternatively could be attached to the subject's skin by adhesives and connected to the remainder of the system by flexible leads. In either case, it is desirable to have good skin-electrode contact as the voltages being measured are relatively small.

Using the electro-oculograph monitor of FIG. 4 with the FIG. 1 system, the processor 14 may be programmed to respond to a change in the direction of gaze of subject 2 by changing the power setting of the trial lens system.

The system of FIG. 1 also includes a cathode ray tube display device 70 which operates under control of the processor 14. The display device 70 comprises conventional cathode ray tube apparatus which is controlled by the processor 14 to display horizontally moving vertical black and white bars 72. Recall, that one type of objective examination for testing visual acuity is the OKN test in which the reflex "following movement" of the eye is monitored as vertical bars are moved horizontally in front of the eye. In the system of FIG. 1, the processor 14 causes the display device 70 to present horizontally moving vertical bars of a predetermined width and the subject is instructed to view the display device through the trial lens system. Depending upon the visual acuity of the subject when looking through the lens system and upon the width of the bars 72, the subject will either exhibit the reflex following movement by following the movement of the bars or he will not. The previously described electro-oculograph monitor detects any movement of the subject's eye and provides a signal indication to the processor 14 of the eye movement. As will be discussed more fully later, the OKN test is advantageously used at various points throughout an eye examination to provide information as to selection of lens system powers to present to the subject. Use of the OKN test in conjunction with the "subjective refinement" test requiring a conscious response by the subject facilitates rapid and accurate determination of the subject's refractive error.

In order to provide a completely automated system and eliminate the need for human intervention in the examination process, it is necessary that provision be made for automatically giving instruction to the subject. This is done in the FIG. 1 system by providing tape player and control unit 80 which, just as in the case of the other apparatus of FIG. 1, operates under control of the processor 14. The tape player is provided with one or more tapes containing pre-recorded messages of instruction. These messages are recorded at predetermined and known locations on the tape so that when a particular message is to be given to the subject 2, the processor 14 simply signals the tape player 80 to position the tape at the desired location, and then signals the tape player to operate to reproduce the desired message. Exemplary messages might include instructions as to how to use the manual response device 16, instructions on selecting preferences between successively displayed symbols, instructions on viewing the screen 6 on which the symbols are projected or the display device 70, etc. Computer control of tape or other recording devices is well known.

Figure 5:
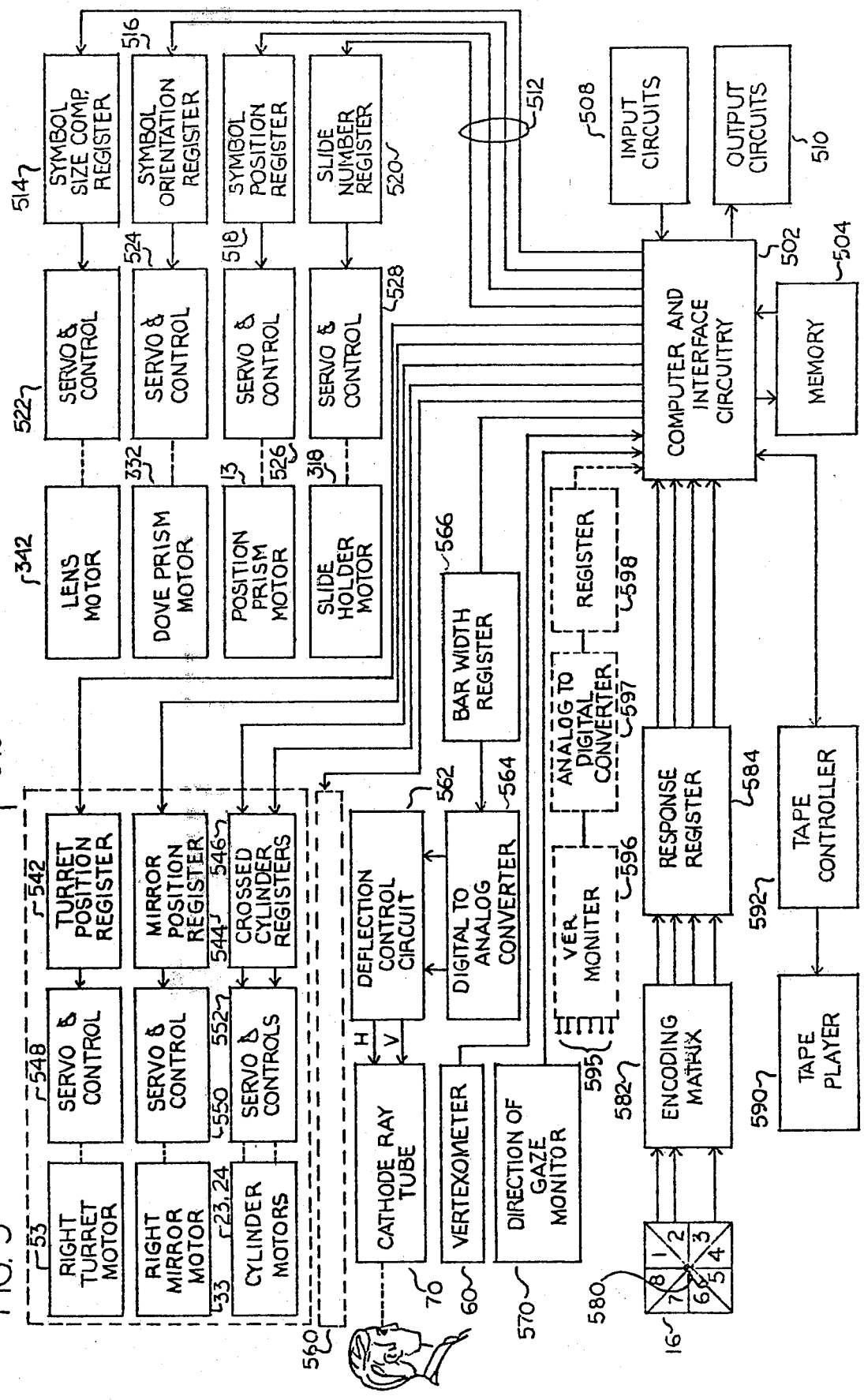
FIG. 5 is a block diagram of one system embodiment of the present invention.

In FIG. 5, the overall system of one embodiment of the present invention is shown in block diagram form. The automatic data processor 14 of FIG. 1 is represented in FIG. 5 by computer and interface circuitry 502 and a memory 504 coupled to the computer. The computer 502 may be any one of a number of available general purpose computers or a special purpose hardwired machine. For example, the computer 502 could illustratively be the PDP-11 made by Digital Equipment Corporation.

The computer 502 communicates with the external world and to the subject 2 via a plurality of external devices. Input information and especially initializing data is supplied by way of input circuit 508 which may comprise any of a variety of input devices such as a tape reader, card reader, typewriter, etc. Such input data indicates the initial settings to be made by the computer 502 of the various items of equipment. The computer 502 communicates with the system operator through the use of output circuits 510. These circuits may comprise any of a variety of computer output displays or recording devices such as a cathode ray tube, a line printer, a typewriter, or other desired device capable of converting the computer output to a form usable by the operator. The memory 504 stores data which is to be processed by the computer 502 and also the programs which control the operation of the computer.

Output signals or commands are supplied by the computer 502 via a plurality of data lines to the external testing equipment. Signals for controlling the operation of the projection apparatus are supplied via lines 512 to various data registers 514 through 520. For example, digital information designating the angular position of the slide holder 18 (FIG. 1) is supplied by the computer 502 to a slide number register 520. This information designates to which angular position the slide holder 18 is to be rotated and thus which size symbol is to be projected onto the screen for viewing by the subject. This information is supplied to a servo and control unit 528 which responds by controlling the angular positioning of a slide holder motor 318 (corresponding to servo motor 318 shown in FIG. 3). Other registers used in controlling the projection apparatus include the symbol size compensation register 514 for receiving digital information designating the magnitude of the size compensation to be made in the projected symbol (to compensate for variations in apparent symbol size due to trial lens system power changes), a symbol orientation register 516 for receiving digital information designating the angular positioning of the displayed Landoldt ring symbol, and a symbol position register 518 for receiving digital information designating the location at which the test symbol is to be displayed. Corresponding servo and control units 522, 524 and 526 respond to such digital information by controlling the operation of corresponding servo motors 342, 332 and 13 (these numerical designations are employed to indicate that the lens motor 342 is the same as the motor 342 of FIG. 3, the dove prism motor 332 is the same as the motor 332 of FIG. 3 and the position prism motor 13 is the same as the motor 13 in FIG. 1). The servo and control units 522, 524, 526 and 528 are identical in construction and are shown in detail in FIG. 6.

Figure 6:
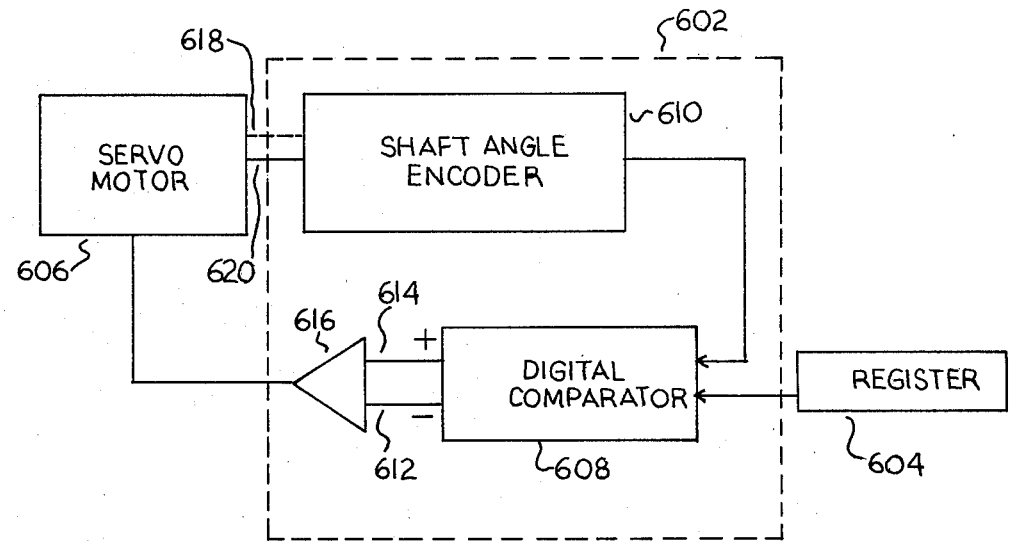
FIG. 6 is a block diagram of a servo and control unit.

A servo and control unit is shown in the dashed line rectangular box 602 of FIG. 6 connected to a register 604, from which digital information is received and to a servo motor 606 which is controlled by the unit 602. The information from the register 604 is applied to a digital comparator 608 and compared with digital information received from a shaft angle encoder 610. The information from the shaft angle encoder 610 identifies the angular position of the drive shaft of the servo motor 606. If the angular position of the shaft of the servo motor 606 is the same as that designated by the information received from the register 604, then the digital comparator 608 produces no output signal. If the position of the drive shaft of the servo motor 606 is at an angle greater than that indicated by the information from register 604, then a signal is provided via lead 612 to an operational amplifier 616 which causes the servo motor 606 to reduce the angular position of its drive shaft by an amount indicated by the signal applied to lead 612. If the angular position of the drive shaft of the servo motor 606 is less than that indicated by the information from register 604, then the digital comparator 608 provides a signal via lead 614 to the operation amplifier 616 which causes the servo motor 606 to increase the angular position of its shaft. In this manner, digital information is used to control the angular position of the drive shaft of a servo motor. Connection 618 between the servo motor 606 and the shaft angle encoder 610 designates a mechanical connection to the drive shaft of the servo motor and connection 620 designates an electrical connection. The structure and operation of servo and control units such as that of FIG. 6 are well known in the art.

Referring again to FIG. 5, the dashed line box 540 represents a portion of the trial lens system used for testing the right eye of the subject. Included is a turret position register 542 for receiving digital information designating the angular position of the right turret 52 of the turret assembly 50 of FIG. 1, a mirror position register 544 for receiving digital information designating the lateral position of the moveable mirror 34 of the mirror assembly 30, also of FIG. 1, and a pair of crossed cylinder registers 546 for receiving information designating the positions of the variable crossed cylinders 27 and 28 of FIG. 2. This information, which is received from the computer 502, is supplied to corresponding servo and control units 548, 550 and 552. These servo and control units control corresponding servo motors 53, 33, and 23, 24 corresponding to the motors 53 and 33 of FIG. 1 and motors 23 and 24 of FIG. 2. The servo and control units 548, 550 and 552 operate in the same manner as that described for the servo and control unit of FIG. 6.

The dashed line box 560 includes apparatus similar to that of the box 540 for use in testing the left eye of the subject.

A cathode ray tube display device 70 for displaying horizontally moving vertical bars is controlled by conventional deflection control circuitry 562 which receives horizontal and vertical deflection control signals from a digital to analog converter 564. The digital to analog converter 564, in turn, receives digital signals from a bar width register 566. Digital information designating the width of the bars to be displayed on the display devices 70 is supplied by the computer 502 to the bar width register 566. The operation of a cathode ray tube display device 70 and associated circuitry may be similar to that of a conventional television set or to that used in digitally controlled conventional CRT's. As indicated earlier, the cathode ray tube display apparatus is provided for conducting OKN tests. Of course, other apparatus might also be used to perform the OKN tests including standard automatically controlled movie projector equipment, a motor-controlled drum having vertical bars on its exterior surface, etc.

A vertexometer 60, corresponding to the vertex distance measuring apparatus 60 of FIG. 1, is provided to detect movement of the head of the subject 2 and to signal the computer 502 accordingly. When such movement is detected by the vertexometer 60, indicating a change in the vertex distance, the computer 502 calculates the effect of such movement on the effective power of the lens system and signals the lens system equipment 540 and 560 to change the power by an amount sufficient to compensate for the movement.

A direction of gaze monitor 570, as also described earlier, is provided to perform two functions. One function is to detect whether or not the subject 2 exhibits the reflex following movement when the OKN test is being performed and to signal the computer 502 accordingly. The other function, as the name indicates, is to monitor the direction of gaze of the subject 2 when test symbols are being displayed at two locations on the test screen so that the power setting of the lens system can be changed when the direction of gaze of the subject 2 changes. The computer 502, in response to a signal from the direction of gaze monitor 570 indicating that the subject 2 has changed his direction of gaze, signals the lens system to make the appropriate change.

For those portions of the eye examination requiring a conscious response by the subject 2, a manual response device 16 is provided for communicating the subject's response to the computer 502. The manual response device 16, also known as a "joy stick", includes a finger 580 manually movable to "point" to any of the eight sectors indicated on the face of the device. Each of the eight sectors corresponds in position to one of the eight locations at which the opening or break in a Landoldt ring is found. Thus, when a Landoldt ring symbol is displayed for viewing by the subject, if the subject is able to see the opening in the ring, he indicates its location by moving the finger 580 toward the sector corresponding to the location of the opening. A signal indicating the sector or angular arc in which the finger 580 is positioned is applied to an encoding matrix 582 which encodes the signal into digital form and supplies it to a digital response register 584. The digital response register 584, in turn, may be sampled selectively by the computer 502 under program control. As will be explained later when describing an illustrative process for using the FIG. 1 and 5 system, the responses made by the subject are utilized by the computer 502 in determining what lens system powers, test symbols, etc., to next present to the subject.

The manual response device 16 is also used by the subject 2 to indicate a preference for one of a pair of test symbols presented at the spaced locations on the screen. If the subject prefers the symbol presented in the left-most location on the screen, he moves the finger 580 to the left and if he prefers the symbol presented in the right-most location, he moves the finger 580 to the right. Again, the manual response device supplies a signal to the encoding matrix 582 indicating the direction in which the finger 580 was moved and this information is ultimately supplied to the computer 502.

Figure 7:
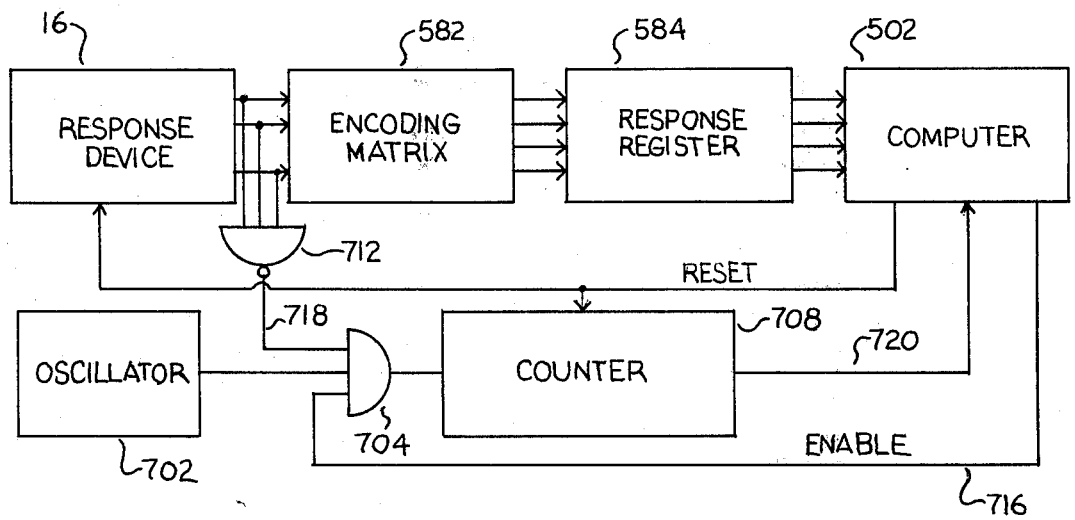
FIG. 7 is a block diagram of apparatus for measuring the response time of a subject.

Alternative manual response apparatus is shown in block diagram form in FIG. 7. With this apparatus, a measure of the time it takes the subject to respond to various test requests is made and this information is utilized by the computer 502 in determining subsequent lens power choices, symbol sizes, etc., to present to the subject. The apparatus includes the previously discussed response device 16, encoding matrix 582, and response register 584 connected to a computer 502. Also included is an oscillator 702 whose output is coupled to an AND gate 704 which, in turn, is connected to a counter 708. The outputs of the response device 16 are coupled to an OR-NOT gate 712 whose output is connected to the AND gate 704. A third input to the AND gate 704 is by way of a lead 716 from the computer 502. The oscillator 702 operates continually to supply a succession of output pulses to the AND gate 704.

When the computer 502 initiates a presentation of test symbols requiring a response from the subject, it applies an enable signal via lead 716 to the AND gate 704. Since, at this time, there would be no output from the response device 16, an output signal is generated by the OR-NOT gate 712 and applied to the AND gate 704 via lead 718. Since signals are being applied to both leads 716 and 718, the pulses generated by the oscillator 702 will be applied via the AND gate 704 to the counter 708 causing the counter to commence counting, i.e., incrementing with each pulse. The counter 708 will continue to count until the AND gate 704 is disabled. This occurs when the response device 16 is operated so that an output signal is applied to at least one of the output leads of the response device causing the OR-NOT gate 712 to terminate generation of an output signal. This results in the disablement of the AND gate 704. With the AND gate 704 disabled, no pulses from the oscillator 702 can reach the counter 708 so that the counter terminates counting.

If the counter 708 does not reach a certain count, i.e., does not "time out", before the subject expresses a preference by operating the response device 16, it is assumed that the subject did not find it difficult in making a choice of one of the alternatives presented to him. If, on the other hand, the counter 708 exceeds some predetermined count, i.e., times out before the subject makes a response, it is assumed that the subject had difficulty choosing between the alternatives presented to him and therefore that the alternatives are about equally acceptable. In this case, the computer determines when a time out occurs by comparing the output of the counter 708 (i.e., the count on the counter) with some threshold count supplied to the computer at the beginning of the examination. Since the reaction times of different subjects will generally be different, a threshold count might be determined for each subject tested by making a few "test runs" and then selecting a threshold count which takes into account the reaction time of the subject. An exemplary threshold count would be the subject's average reaction time, determined by the test runs, plus three times the standard deviation of the average (using, for example, the well-known normal distribution).

As will be discussed later, the action taken by the computer 502 after presentation of symbols requiring a response depends upon whether or not there was a time out. After the subject's response time has been measured, the computer 502 applies a reset pulse both to the response device 16 and to the counter 708 in preparation for the next subject response time measurement.

Instructions for guiding the subject 2 in using the manual response device 16 and generally in taking the examination are given by a tape player 590 (FIG. 5). The tape player 590 includes one or more tapes containing pre-recorded messages of instruction for the subject. When a particular message is to be given to the subject, the computer 502 applies a signal to a tape controller 592 identifying the desired message and the tape controller signals the tape player 590 to properly position the tape and reproduce the desired message.

As can be seen from the above discussion, very little if any human intervention is required in conducting an eye examination with the system of the present invention. Even if some human assistance is desired, it would be of a type which a trained technician could do relieving the ophthalmologist from much of the time consuming routine required with currently used methods. Such assistance might include, for example, instructing the subject as to where he is to sit, positioning the lens system with respect to the subject, and generally making the subject feel at ease.

An alternative to use of the manual response device 16 of FIG. 5 for indicating a preference between symbols, is a VER monitor 596. (It is shown in dashed-line boxes to indicate that it is an alternative to the manual response device 580.) The monitor 596 includes a plurality of electrodes 595 which are secured to the scalp of the subject 2 for detecting the electrical activity (signals) in the occipital lobe of the brain. The detected signals are amplified by the monitor 596 and applied to an analog to digital converter 597 which converts the signals to digital form. The digital signals are then supplied to a register 598 which is selectively sampled by the computer 502. These signals represent (in digital form) an electroencephalogram of the subject. The computer 502 processes the signals to determine the clarity and sharpness with which the subject was able to perceive the pairs of test symbols presented to the subject. The relation of the visual acuity of the subject to the amplitudes of these signals was described earlier. In this manner, an unconscious response by the subject 2 is detected by the VER monitor 596 and communicated to the computer 502.

In operation, the system of FIG. 5 is set in motion by the operator through the input circuits 508. These input circuits are utilized together with the programmed control of the computer 502 to cause the test equipment to generate test stimuli on the screen 6 (FIG. 1) and on the face of the cathode ray tube display device 70. These test stimuli are viewed through the lens system whose power is modified from time to time in accordance with responses and actions from the subject communicated to the computer 502 by the manual response device 16, the direction of gaze monitor 570, the vertexometer 60, and the VER monitor 596. The response or action of the subject is then dynamically used by the computer 502 in the selection of subsequent stimuli to present to the subject, in selecting the lens system power to present to the subject and in making previously described compensation for changed testing conditions, e.g. change in vertex distance. When the testing is complete, as determined by the program, the computer 502 generates and applies output data to the output circuits 510 specifying the results of the test, including eye wear prescription and vertex distance.

Figure 8A:
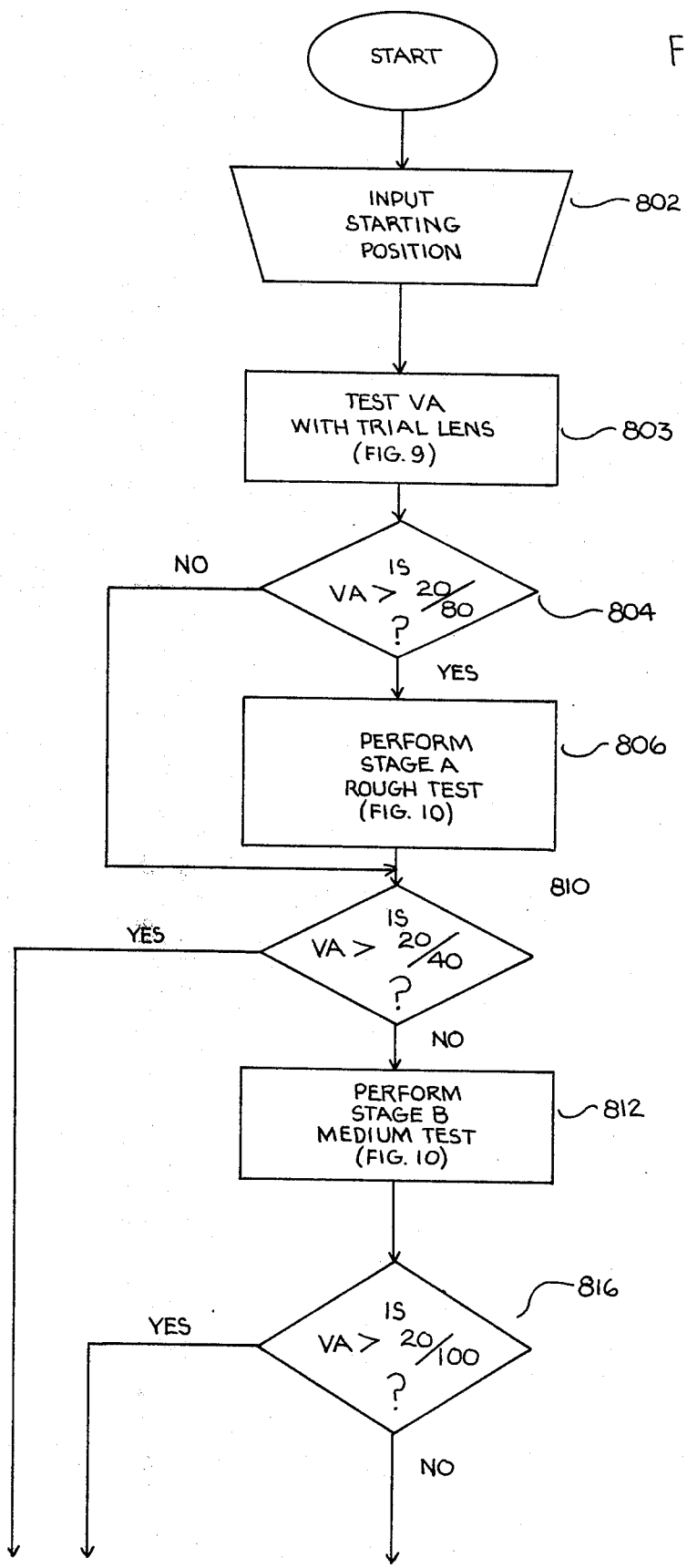
Figure 8B:
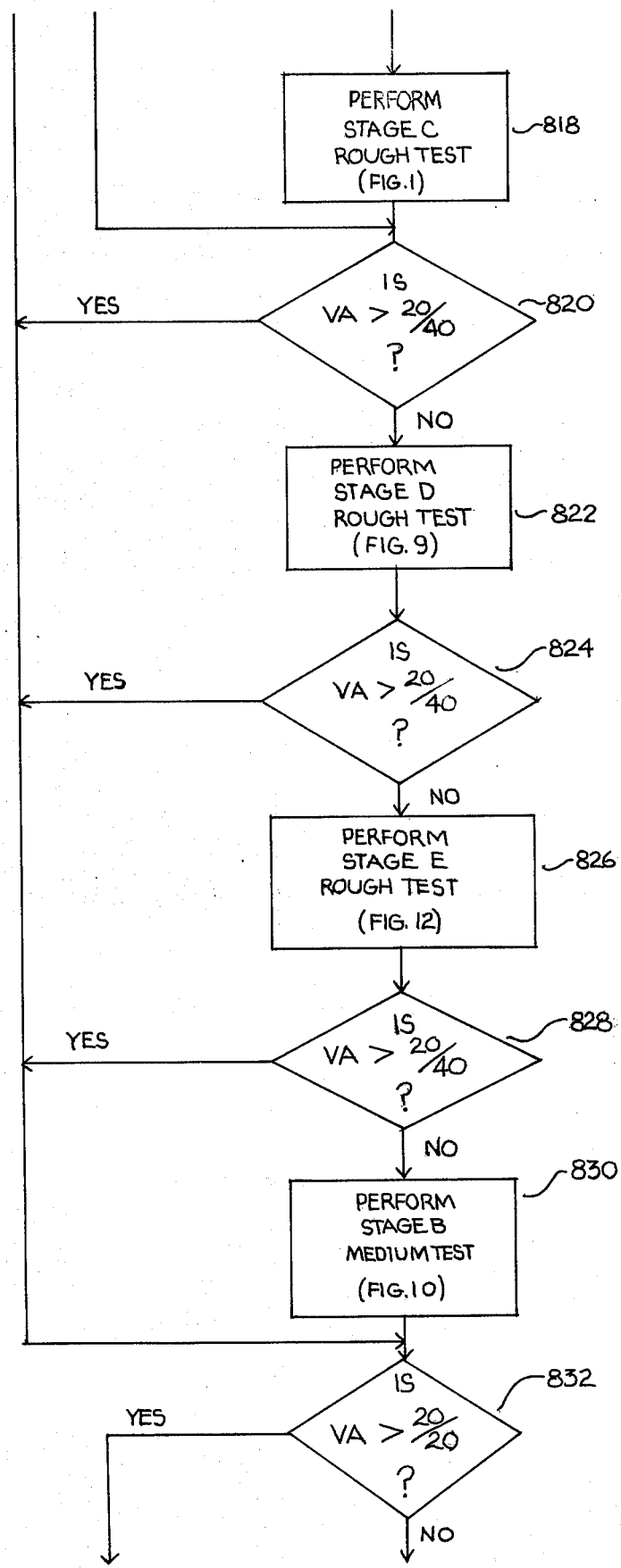

Referring now to FIGS. 8A, 8B and 8C, the overall method of one embodiment implemented by the computer program of computer 502 is illustrated in a flow chart. Generally, the examination is started by the operator when input starting data is supplied via the input circuits 508 to the computer 502. This input starting data might consist of the subject's old eye glass prescription, provided he had an old prescription, a rough prescription determined by the method of retinoscopy as discussed earlier, or a prescription determined by some other conventional procedure. After the input starting data is applied to the computer, the subject is positioned behind the lens system and the vertexometer 60 (FIGS. 1 and 5) is initialized, i.e., either the vertexometer 60 is conditioned to maintain a fixed vertex distance, or the computer 502 is supplied with an indication of the initial vertex distance to enable any subsequent changes in this distance to be monitored by the computer. The computer 502 is then placed in operation to perform the examination under control of the program.

The first step in the program, as indicated by block 803 of FIG. 8A, is to call a subprogram to test the visual acuity of the subject with the power setting then present in the trial lens system. This test is conducted in accordance with the subprogram whose flow chart is shown in FIG. 9A and 9B. This subprogram provides for testing the visual acuity of the subject utilizing Landoldt rings and the OKN test.

The power setting of the trial lens system at this stage of the process will be that corresponding to the input starting prescription indicated in block 802. The first step of the FIG. 9A subprogram, as indicated in block 902, is to determine whether or not the visual acuity of the subject had previously been tested in the examination and if so whether an OKN response had been elicited (i.e., whether the subject exhibited the above-described reflex following movement). If the visual acuity of the subject had not previously been tested, then, as indicated in block 904, a Landoldt ring test is performed. The subprogram for the Landoldt ring test is illustrated in FIG. 9B, the first step of which involves the selection of a test symbol size corresponding to the then current visual acuity measurement of the subject (block 950). Recall that one subjective test for determining the visual acuity of the subject involves the presentation to the subject of different size Landoldt ring symbols and determining for which size the subject is able to specify the location of the break in the ring. The particular size of the Landoldt ring symbol for which the subject is able to do this defines a visual acuity for the subject. In step 950 of FIG. 9B, the reverse of this is carried out in that the symbol size corresponding to the subject's current visual acuity (i.e., visual acuity with the current power setting of the lens system) is selected. After the appropriate symbol size has been selected, the computer 502 causes the projection apparatus to successively display a series of randomly oriented symbols of the selected size as indicated by block 952. As each symbol is displayed, the subject is requested to indicate the location of the break in the ring. After a series of symbols has been presented, e.g. six, and the responses to such presentations recorded, the computer determines whether or not two thirds or more of the symbol orientations were correctly determined by the subject (block 954). If they were, the symbol size is decreased, for example, by an amount corresponding to the change in size of symbols from one line of the well-known Snellen chart to a next adjacent line (block 956) and the subprogram returns to block 952 where a series of symbols are again presented to the subject. If the subject did not determine at least two thirds of the symbol orientations correctly, then the subprogram of FIG. 9B moves to block 958. In block 958, the determination is made as to whether, just prior to the previous presentation of symbols, the symbol size had been decreased or increased. If it had been decreased, then the subprogram returns to block 906 of FIG. 9A, otherwise the subprogram moves to block 960 of FIG. 9B. In the step represented by block 960, a determination is made as to whether or not the symbol size is maximum and if it is, the subprogram sets visual acuity equal to 20/800 (block 961), then returns to block 906 of FIG. 9A; if it is not, the subprogram moves to block 962 where the symbol size is increased by an amount corresponding to a one-line change on the Snellen chart. After the increase in symbol size, then a series of such symbols are again presented to the subject as indicated in block 952 and the process is repeated.

The visual acuity of the subject is determined in the Landoldt ring test of FIG. 9B by that size of a test symbol whose orientation the subject is just able to determine two thirds or more of the time. Each symbol size, as already indicated, defines a visual acuity measure.

In block 906 of FIG. 9A a determination is made as to whether the visual acuity determined by the Landoldt ring test is greater or less than 20/800. If it is less than that, then the subprogram of FIG. 9A return to block 804 of FIG. 8A, otherwise it moves to block 908 of FIG. 9A. As indicated by block 908, an OKN test is performed with the vertical bar width selected to correspond to one half the visual acuity of the subject determined in block 904. (Recall that in the OKN test, the bar width at which a subject exhibits the reflex following movement defines a certain visual acuity). The subject is requested to view the cathode ray tube display device 70 and if a response is elicited, as determined by the direction of gaze monitor, the subprogram of FIG. 9A moves from block 910 to block 914 otherwise it moves to block 912. In the step represented by block 912, the computer sets a flag indicating that only the Landoldt ring test is to be used thereafter and not the OKN test. The subprogram then returns to block 804 of FIG. 8A. In the step represented by block 914 of FIG. 9A, the current visual acuity measure of the subject is set equal to that determined by the Landoldt ring test of block 904 and the subprogram moves to block 916.

Returning now to the decision block 902, if it had there been determined that the visual acuity of the subject had been tested and that an OKN response had been elicited, then the process would have moved to block 916. In block 916, the OKN bar width is set to correspond to the current visual acuity measure of the subject — either that existing upon entering the subprogram of FIG. 9A or that established in block 914. The OKN test is then performed as indicated in block 918 and a determination is made as to whether a response was elicited from the subject (block 920). If a response was elicited, the bar width is decreased, e.g. by one half, (block 924) and the OKN test is again performed. This cycle continues until a bar width is selected which does not produce a response from the subject in which case the subprogram moves to block 922 where the bar width is increased, e.g. by one half, and then to block 926 where a determination is made as to whether or not the bar width is at its predetermined maximum. The process could also reach block 926 if the initial determination in block 920 had been "No." If the bar width is maximum, the visual acuity is set to 20/800 (block 931) and the process returns to block 804 of FIG. 8A, otherwise it moves to block 928 of FIG. 9A. In the step represented by block 928, a determination is made as to whether the bar width, just prior to the increase in the width in block 922, had been decreased and if it had, the process returns to block 804 of FIG. 8A. If it had not been decreased just prior, then the OKN test is again performed (block 918) and the previously described operation repeats. The purpose of the functions performed in blocks 918, 920, 922, 924, 926 and 928 is to determine the visual acuity of the subject using the OKN test with the trial lens system set at a certain power.

Returning once again to block 902 of FIG. 9A, if it is determined that the visual acuity of the subject has previously been tested but that no OKN response was elicited, then the process moves to block 930 where the Landoldt ring test is performed in accordance with the subprogram of FIG. 9B as previously described.

After block 803 of FIG. 8A is completed as indicated in FIGS. 9A and 9B, block 804 is to determine whether the visual acuity of the subject, based on the results obtained in block 803 is less than or greater than 20/80. If the visual acuity is less than 20/80, the program moves to block 806 where a so-called stage A rough test subprogram is called. This subprogram is illustrated in FIG. 10 which shows a general flow chart of three different subprograms or tests including the stage A rough test, a stage B medium test and a stage I fine test. For the stage A test, a variable N is set equal to 2 as indicated at the top of FIG. 10. (As also indicated, stages B and I differ from stage A and from each other only in the value assigned to the variable N). The purpose of the stage A rough test, as the name implies, is to make a rough determination of an eyeglass prescription for correcting the subject's refractive error.

The first step of the stage A subprogram is to calculate the value of another variable $\Delta D$ which represents a change in the spherical power of the lens system from a so-called current reference prescription (CRP) to be used in the test. At this stage of the process, the CRP corresponds to the starting prescription initially applied as input data to the computer. The CRP will change in the course of performing the eye examination dependent upon responses elicited from the subject. The value of $\Delta D$, calculated in block 1002, is $1/(N \cdot VA)$, where $N=2$, as previously indicated, and VA represents the visual acuity of the subject determined from the input starting data. After $\Delta D$ is calculated, two trial prescriptions P1 and P2 are calculated as indicated in block 1004, with $P1 = CRP + \Delta D$ and $P2 = CRP - \Delta D$. In the next step, represented by block 1006, the subject is instructed to view a test symbol at two spaced locations on the test screen and to indicate a preference between the symbols based on the visual sharpness and clarity of the symbols. The lens system is controlled by the computer to present a power of P1 for the symbol presented at one of the locations and a power of P2 for the symbol presented at the other location. As already described, the lens system power may be automatically changed when the subject changes his direction of gaze from one of two simultaneously presented symbols to the other or the computer may automatically cause the presentation of the test symbol alternately at the two locations requiring the subject to involuntarily change his direction of gaze to view the symbol being displayed. When the subject indicates his preference (either consciously by using the manual response device 16 or unconsciously by way of the VER monitor 596) the computer records the lens system power preferred by the subject as PP. A decision is then made as to whether or not there was a sign reversal as indicated by block 1008. A sign reversal occurs when the subject had previously indicated preferences for steadily increasing or decreasing lens system powers and then indicated a preference for a lens system power which was either a decrease or increase respectively. For example, if the subject had indicated preferences for steadily increasing lens system powers and then expressed a preference for a lens system power which was a decrease from the previous preference, this would constitute a sign reversal. Since, at this stage of the process, the subject has only indicated one preference, there would be no sign reversal so that the program would move to block 1010. If, further along in the process, there is a sign reversal at block 1008, then the computer calculates a new current reference prescription in accordance with the formula of block 1012 of FIG. 10. The term CRP(New) represents the new current reference prescription; the term CRP(Old) represents the old current reference prescription; and the term PP represents the preferred one of the trial prescriptions P1 or P2 of block 1004.

At block 1010, a decision is made as to whether or not a time out occurred before the subject indicated a preference between the trial prescription P1 and P2. Recall that in one embodiment of the manual response apparatus, timing circuitry was included to provide the computer with a measure of the reaction time of the subject. Thus, if in the subprogram of FIG. 10, the subject fails to express a preference between the trial prescriptions P1 and P2 within a certain predetermined period of time, visual acuity is tested by the subprogram of FIG. 9 as indicated at block 1013. The subprogram then terminates and the process returns to block 810 of FIG. 8A. If no time out occurs, then the subprogram moves to block 1014 where the new current reference prescription is calculated in accordance with the formula indicated in the block. The subprogram then returns to block 1004 where two new trial prescriptions P1 and P2 are calculated as previously described. The process is then repeated until at some time in the subprogram of FIG. 10, the subprogram concludes and returns to block 810 of FIG. 8A.

Regardless of the route taken through the FIG. 9A subprogram, the visual acuity measure of the subject will be made with the current trial lens system setting and a determination made at block 803 of FIG. 8A as to whether the visual acuity is less than 20/80 or not. If the acuity exceeds or equals 20/80, the process moves to block 810. If the acuity is less than 20/80, the stage A test is performed in block 806, as detailed in FIG. 10. When this stage A is completed, the visual acuity is again determined as before by the subprogram of FIG. 9 as indicated in block 1013 of FIG. 10. The process then moves to block 810 of FIG. 8A. If at block 803 or at 1013 of FIG. 10, the visual acuity is determined to be better than 20/40, the process moves to block 832 of FIG. 8B. If, at block 810, the visual acuity is less than 20/40, the process moves to block 812 where a stage B medium test is performed. This test is the same as the previously described stage A test of FIG. 10 except that the variable N is set equal to 4 rather than 2. The significance of the value 4, as opposed to the value 2, for the variable N is that the change in lens system power presented to the subject is in a smaller increment. That is, the greater is the value of the variable N, the smaller is the incremental change in the lens system power.

After the stage B test is performed and the visual acuity is determined, a determination is made as to whether this visual acuity is better than 20/100 and if it is, the process moves to block 820. If it is not, the process moves to block 818 where a stage C rough test is performed. This test is illustrated by a flow chart in composite FIG. 11 which also represents stage D, G and J tests to be described later.

The process for performing the stage C, D, G and J tests is the same except that the values assigned to four variables N1, N2, N3, A and B are different for each test. For the stage C test, the values of the variables are indicated in the first column under the letter C in the table shown at the top of FIG. 11A. Specifically, variable N1 has a value of 4, variable N2 has a value of 2, variable N3 has a value of 2, variable A has a value of 90°, and variable B has a value of 0.25. The angle designated by the variable A represents an angular distance of the lens system trial cylinder (i.e., the variable crossed cylinder combination of FIG. 2) measured in a standard cartesian coordinate system fixed in the subject's frontal plane.

The function of the stage C rough test is to make a rough determination of the subject's astigmatic axis (if any exists). In the first step of the test, represented by block 1102, a determination is made as to whether the current reference prescription contains a cylinder component, i.e., any cylindrical power along with the spherical power. At this stage of the test, no cylinder component would be present in the current reference prescription unless the subject's old prescription had contained such a component. If no component is present, the process moves to block 1106 where two new trial prescriptions are calculated, one having a cylinder component whose axis is oriented at A=90° (vertical) and the other having a cylinder component whose axis is oriented at A+90°=180° (horizontal). The cylindrical power of each new trial prescription in $1/N_2VA$, as indicated in block 1106, and the spherical power is $CRP-1/N_1VA$, a value sufficient to compensate for the added cylindrical power so that the resultant spherocylindrical power of the two trial prescriptions is the same as the current reference prescription.

The two new trial prescriptions are then presented to the subject in the manner already discussed and if one is preferred it is recorded as P.P. (block 1108). If in block 1102 it had been determined that the current reference prescription contained a cylinder component, then two new test axes for the cylinder component are calculated as indicated in block 1104, where CA represents current axis and D represents the power of the cylinder component. These two test axes would be presented to the subject to ascertain his preference (block 1108) and any preference would be recorded as P.P. After the two alternatives are presented to the subject (whether they be the two new trial prescriptions or the new test axes for the cylinder component), a determination is made as to whether a preference was expressed before a time out (block 1110). If not, the process returns to block 820 of FIG. 8B. If so, the process moves to block 1112 of FIG. 11B.

Figure 11A:
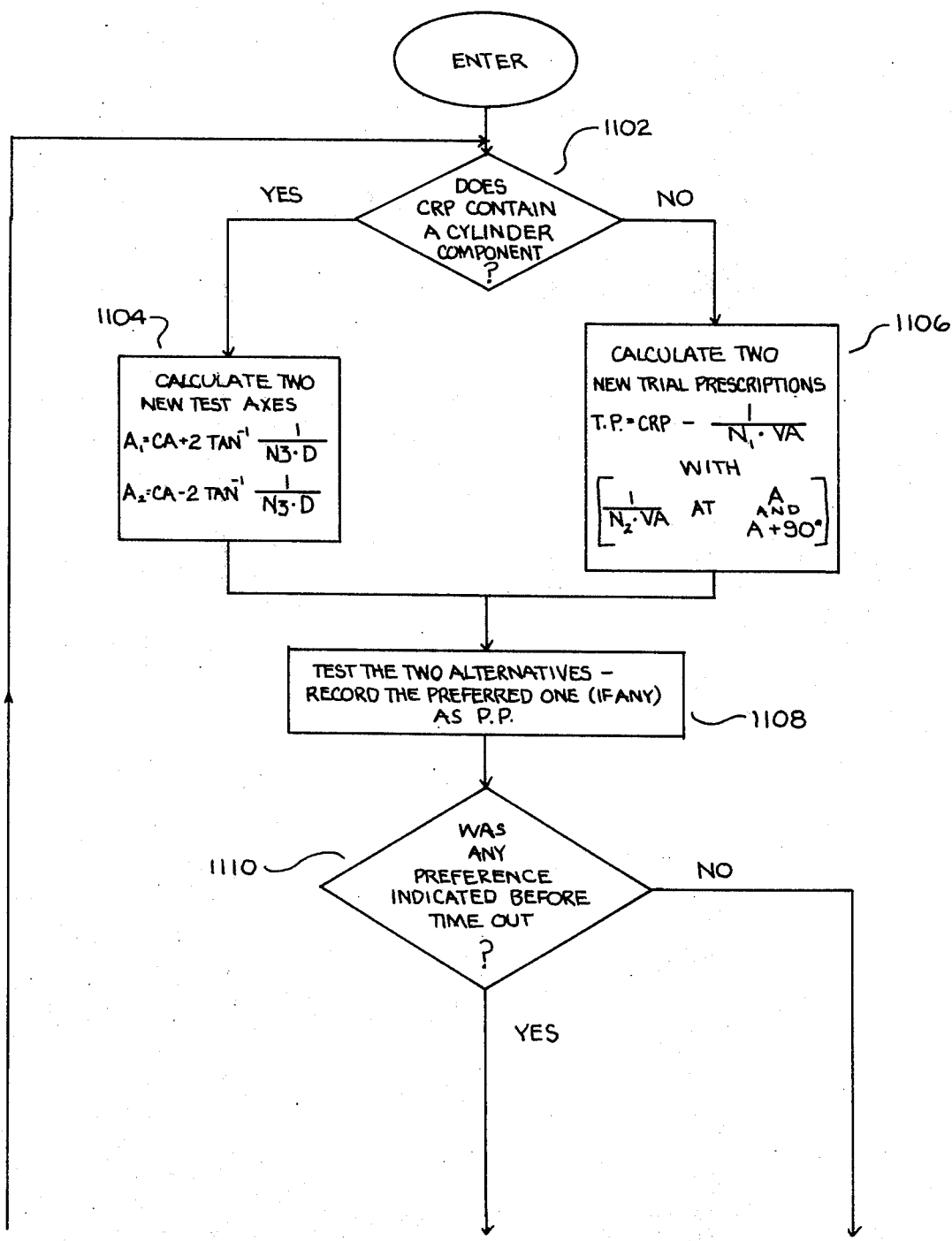
Figure 11B:
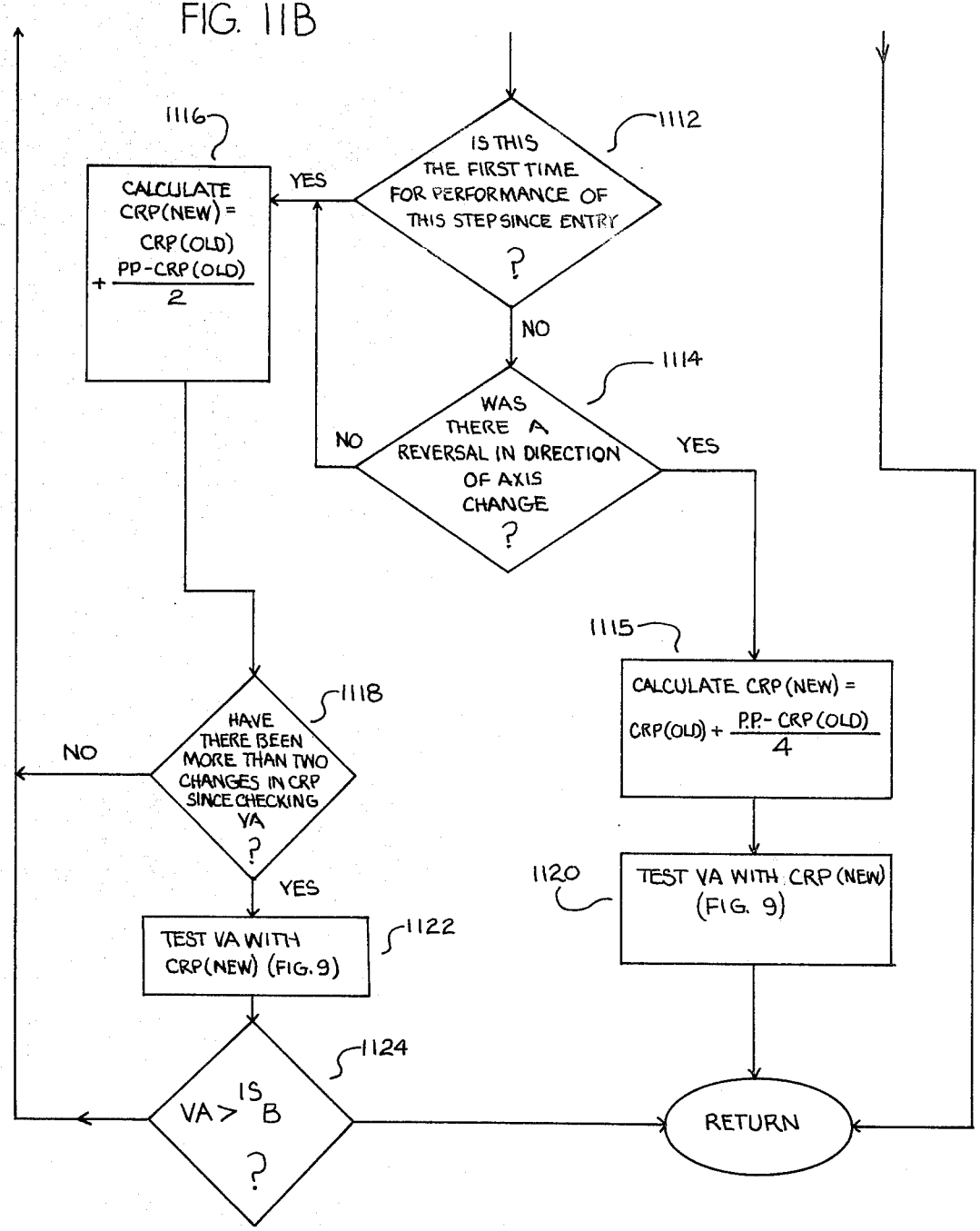

The function of the step represented by block 1112 is to determine if the subprogram of composite FIG. 11 had previously gotten as far as block 1112 since the calling of the subprogram, i.e., whether this performance of the step of block 1112 is the first since entry in the subprogram. If the step had been performed previously, the process moves to block 1114 where a determination is made as to whether there was a reversal in the direction of cylinder axis change with the last preference expressed by the subject. The meaning of this can best be understood by way of example. Assume that for successively presented pairs of cylinder axis positions, the subject each time indicates a preference for the axis position which is at an angle greater than that of the immediately preceding preference, and than that the subject finally indicates a preference for an axis position which is at an angle less than that of the previous preference. This constitutes a "reversal in the direction of cylinder axis change." If it is determined in block 1114 that such a reversal has occurred, the process moves to block 1115 where a "new" current reference prescription is calculated in accordance with the formula shown in the block. With the trial lens system set at this prescription, the subject's visual acuity is tested, as indicated in block 1120, as described earlier in connection with FIGS. 9A and 9B. The subprogram of FIGS. 11A and 11B then returns to block 820 of FIG. 8B.

If it had been determined in either block 1112 that the step represented by the block had not been previously performed since entry or in block 1114 that no reversal had occurred, then the process would have moved to block 1116 for calculation of a new current reference prescription. The only difference between the current reference prescription calculated in block 1116 and that calculated in block 1115 is that the latter constitutes a smaller change from the "old" CRP than does the former. The significance of this is that in the latter case, the examination is getting closer to determining the prescription necessary to correct the subject's astigmatic error and these smaller changes are warranted so as not to "overshoot" the ultimate prescription desired. After the new CRP is calculated in block 1116, the program moves to block 1118 and then, if there have been more than two changes in the CRP since testing the subject's visual acuity, on to block 1122, otherwise it returns to block 1202. In block 1122, the subject's visual acuity is tested with the new COP. The next step (block 1124) is to determine if the subject's visual acuity is better than the variable B, which for the stage C test is set equal to 0.25. If it is, the program returns to block 820 of FIG. 8B, otherwise the program returns to block 1102.

Returning now to the general program of FIG. 8B, and in particular to block 820 which represents the next step following the performance of the stage C rough test, there it is indicated that a determination is made as to whether the subject's visual acuity (with the CRP) is better than 20/40. If it is, the program moves to block 832, and if it is not, the program moves to block 822 where a stage D rough test is performed. Except for the value at which the variables N1, N2, N3, A and B are set, the stage D rough test is the same as the stage C test just described.

At this point, a comment might be made regarding the selection of the axis of the cylinder component. Although not shown in the flow charts, provision might be made for making a determination as to whether the axis of the cylinder component has, through preferences expressed by the subject, been moved through 180°. If it has, then the cylinder axis may be fixed simply at that position where the subject's visual acuity is maximum or the cylinder may be eliminated altogether should the visual acuity not change with changes in the cylinder axis. With the illustrative method disclosed, in which choices are based on visual acuity, the above-mentioned provision may be unnecessary.

Figure 12A:
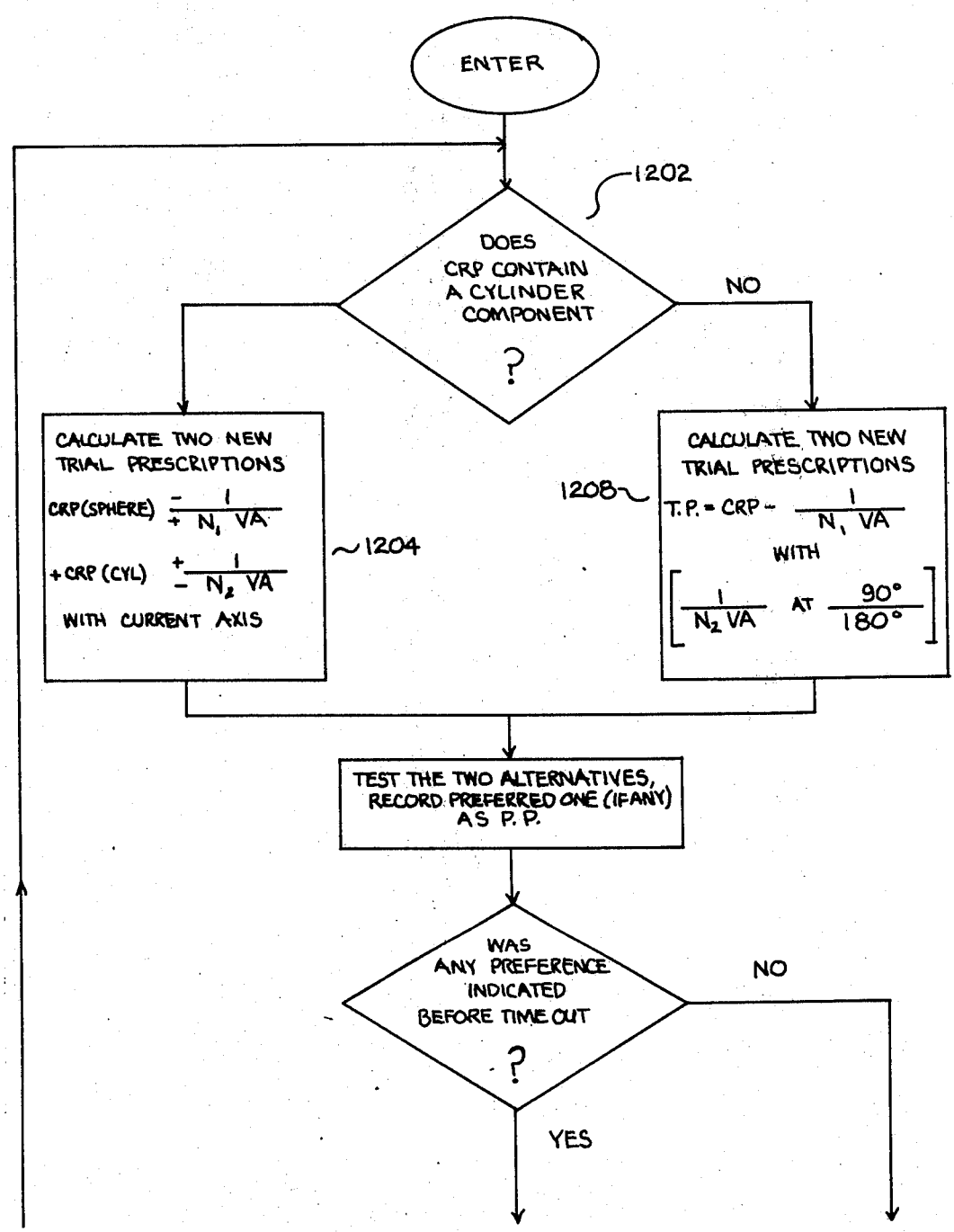

After performing the stage D test, a determination is again made as to whether the subject's visual acuity is greater than 20/40 as indicated in block 824. If it is, the program moves to block 832, and if it is not, the program moves to block 826 where a so-called stage E rough test subprogram is called. This subprogram is illustrated by flow chart in composite FIG. 12. The FIG. 12 flow chart also represents so-called stages H and K tests with the only difference between these tests and the stage E test being the value of variables N1, N2, and B as shown in the table at the top of FIG. 12A. The function of the FIG. 12 subprogram is to assist in determining the power of the subject's astigmatic error, if any. A comparison of the composite FIG. 11 subprogram with the composite FIG. 12 subprogram reveals that the two subprograms contain the same number of steps, most of which are identical. The principal difference is between block 1204 of FIG. 12A and the corresponding block 1104 of FIG. 11A in which in the former, two new trial prescriptions are calculated to provide the cylinder component with new alternative power settings whereas in the latter, two new test axes are calculated. In view of the similarities between the two subprograms, no detailed discussion will be given of the FIG. 12A and 12B subprogram.

Figure 12:
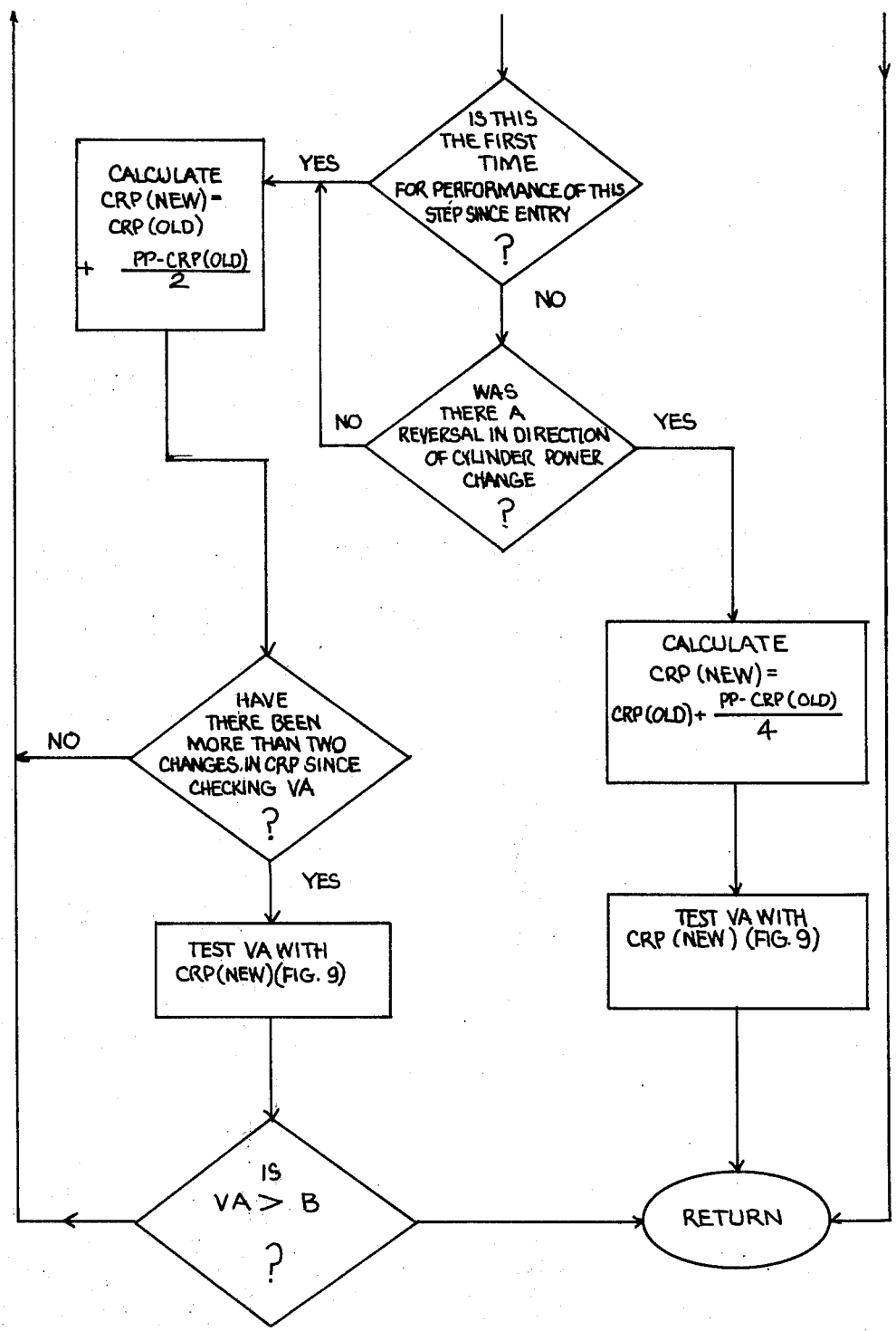

After performing the stage E rough test of composite FIG. 12, the process of composite of FIG. 8 proceeds to block 828 where a determination is again made as to whether the subject's visual acuity is greater than 20/40. If it is, the process moves to block 832 and if it is not, the process moves to block 830 where a stage B medium test is performed. This test is illustrated by flow chart in FIG. 10 which was discussed earlier in conjunction with the stage A test. In the stage B test, the variable N is set equal to 4 rather than 2 as in the stage A test.

If, in any of the steps represented by blocks 810 of FIG. 8A, 820, 824 or 828 of FIG. 8B, it is determined that the subject's visual acuity is better than 20/40, or after performing the stage B medium test of block 830, the process moves to block 832 of FIG. 8B. There, a determination is made as to whether the subject's visual acuity is better than 20/20. If it is, the process moves to block 840 of FIG. 8C, otherwise the process moves to block 834 of FIG. 8C. In block 834, a stage G medium test is performed in accordance with the flow chart of composite FIG. 11 already described. After the stage G medium test, the process again makes the determination at block 836 as to whether the subject's visual acuity is better than 20/20. If it is determined that it is not, the process moves to block 838 where a stage H medium test is performed in accordance with the flow chart of FIG. 12. If visual acuity at block 836 exceeds 20/20, the process moves to block 840. Next, in order, a stage I fine test is performed in accordance with the subprogram of FIG. 10, a stage J fine test is performed in accordance with the subprogram of composite FIG. 11, and a stage K fine test is performed in accordance with the subprogram of composite FIG. 12 (block 840). A determination is then made at block 842 as to whether the subject's current reference prescription has changed since the most recent entry of block 840 and if it has, the tests shown in block 840 are again performed, otherwise the process causes the computer system to generate the output data (block 844) obtained from performing the eye examination. This output data would consist of a lens prescription together with a vertex distance for correcting the subject's refractive error and, if desired, the subject's visual acuity with the trial lens system set at the final prescription. This information, of course, would be provided for both eyes of the subject.

In the manner shown and described, apparatus and method are provided for performing refractive error measurement under conntrol of a programmed automatic data processing system. As illustrated in the program represented by the flow chart of composite FIG. 8 and the subprograms represented by the flow charts of FIGS. 9 through 12, both objective and subjective eye tests are performed under control of the data processing system in determining the subject's refractive error. The power of the trial lens system of the apparatus may be varied in a continuous manner, also under control of the data processing system, to provide a wide range of lens powers which may be presented to the subject while maintaining constant the number of lenses which are placed before the subject. Visual stimuli are automatically presented to the subject for viewing through the trial lens system and the subject is instructed as to use of a manual response device for responding to the stimuli. Some of the stimuli consist of pairs of symbols successively presented at two locations on a screen for which the subject is to indicate a preference for one symbol of each pair. Even though the power of the trial lens system may be different for viewing one symbol of the pair from that for viewing the other symbol, the apparent symbol size is automatically maintained constant to thereby eliminate what might otherwise be a preference bias by the subject for larger size symbols. The subject's responses to the test stimuli presented are utilized by the data processing system in determining subsequent test stimuli to present to the subject.

Although the invention has been described with reference to particular preferred embodiments thereof, many changes and modifications will become apparent to those skilled in the art in view of the foregoing description which is intended to be illustrative and not limiting of the invention defined in the appended claims.

What is claimed is:

1. In an automatic process for subjectively determining the refractive error of a subject wherein the power of lenses of a trial lens system presented to the subject is controlled by a data processing system in response to responses derived from the subject choosing between choices of images presented to the subject until an optimum lense power is determined and thereafter providing a readout of a lense prescription which provides refractive correction for the subject, the improvement comprising the steps of:
   a. determining under control of the data processing system the visual acuity of the subject when viewing test stimuli through a trial lens system set at a selected power,
   b. presenting test stimuli for viewing by the subject through the trial lens system set alternatively at the selected power $+\Delta D$ and at the selected power $-\Delta D$, where $\Delta D$ has a first value if the visual acuity is determined in step(a) to be greater than a predetermined threshold value and where $\Delta D$ has a second value greater than said first value, if the visual acuity is determined in step (a) to be less than the threshold value, c. determining under control of the data processing system whether one of the trial lens system power settings of selected power $+\Delta D$ or $-\Delta D$ is preferred by the subject over the other for viewing the test stimuli, and d. repeating steps (a) – (c) above at frequent intervals during the process.

2. A process as in claim 1 wherein step (a) includes the steps of:

d. determining under control of the data processing system the visual acuity of the subject with the trial lens system set at a selected power using the Landoldt ring test, e. displaying moving bars to the subject, f. monitoring under control of the data processing system the direction of gaze of the subject to determine if the subject's eyes exhibit a reflex following movement with the moving bars, and g. if the subject's eyes exhibit a reflex following movement, determining under control of the data processing system the visual acuity of the subject with the trial lens system set at a power of D using the optokinetic nystagmus test, and h. if the subject's eyes do not exhibit a reflex following movement, setting a flag indicating that no reflex following movement was exhibited.

3. A process as in claim 2 wherein step (e) comprises displaying the moving bars on a cathode ray tube.

4. A process as in claim 2 wherein step (f) comprises monitoring the changes in the electric field surrounding the eyeballs of the subject caused by the shifting corneal-retinal standing potential.

5. A process as in claim 1 wherein step (b) includes the steps of:

i. presenting under control of the data processing system a test symbol alternately at first and second spaced locations on a screen, and j. setting under control of the data processing system the power of the trial lens system at the selected power $+\Delta D$ when the symbol is presented at the first location and at the selected power $-\Delta D$ when the symbol is presented at the second location.

6. A process as in claim 1 wherein step (b) includes the steps of:

k. presenting under control of the data processing system a test symbol simultaneously at first and second spaced locations on a screen, l. monitoring the direction of gaze of the subject, and m. changing under control of the data processing system the power the trial lens system from the selected power $+\Delta D$ to the selected power $-\Delta D$ when the subject's direction of gaze shifts from the first location toward the second location and from the selected power $-\Delta D$ to the selected power $+\Delta D$ when the subject's direction of gaze shifts from the second location toward the first location.

7. A process as in claim 1 wherein step (b) includes modifying under control of the data processing system the size of the test stimuli presented so that the apparent size of the stimuli when viewed by the subject through the trial lens system set at a selected power $+\Delta D$ is the same as the apparent size of the same stimuli when viewed by the subject through the trial lens system at a selected power $-\Delta D$.

8. A process as in claim 1 wherein the subject indicates a preference for one of the trial lens system power settings by operating a manual device.

9. A process as in claim 8 further including the steps of n. maintaining a measure of the time elapsed from initial presentation of a test stimuli, and o. terminating presentation of the test stimuli if the subject fails to indicate a preference within a certain period of time as measured in step (n).

10. Apparatus for measuring refractive error of a subject comprising:

display means for displaying test symbols, a trial lens system continuously variable over a range of powers through which the subject views the displayed test symbols, control means for setting said trial lens systems at any selected power setting within said range of powers, a manual response device operable by the subject for providing a plurality of output signals, objective means for objectively determining the visual acuity of the subject for any discrete power setting of the trial lens system and providing an output signal indicating the test results, display means for indicating the refraction error, if any, of the subject, data processing system means coupled to said response device, said display means, said control means, said objective refraction means and said display means and responsive to signals received from said response device and said objective refraction means to control the control means to set the trial lens system at discrete settings of cylinder and spherical power which provide a refractive correction most desired by the subject and control the display means to indicate the test results.

11. Apparatus as in claim 10 wherein said trial lens system comprises first and second lenses coaxially positioned a fixed distance apart, and means for varying the effective distance between the first and second lenses in a continuous fashion.

12. Apparatus as in claim 11 wherein said varying means comprises first reflective means positioned between said first and second lenses for reflecting in a direction lateral to the axis of the first and second lenses light traveling along the axis of the lenses from the displayed symbols through said first lens, second reflective means positioned laterally of the axis of the lenses and movable, under control of the data processing system, toward or away from the axis, for reflecting light received from said first reflective means back toward the axis of the lenses, and third reflective means positioned between the first reflective means and the second lens for reflecting light from the second reflective means toward the second lens.

13. Apparatus as in claim 12 wherein said first reflective means comprises a first planar mirror positioned so that the plane of the mirror is at an angle of substantially 45° with the axis of the lenses, wherein said second reflective means comprises a pair of planar mirrors, a first of which is positioned so that its plane is substantially parallel with the plane of the first mirror and a second of which is positioned so that its plane forms substantially a right angle with the first mirror of the pair, and wherein said third reflective means comprises a fourth planar mirror positioned so that its plane forms substantially a right angle with the said first mirror and is substantially parallel with the plane of the second mirror of said pair.

14. Apparatus as in claim 11 wherein said trial lens system further comprises turret means comprising a plurality of lenses, including said first lens, spaced about the periphery thereof, said turret means being rotatable, under control of the data processing system, to selectively position any one of said plurality of lenses coaxially with said second lens.

15. Apparatus as in claim 10 further including means, operable under control of the data processing system, for varying the size of the test symbols displayed so that the apparent size of the symbols when viewed by the subject through the trial lens system remains constant regardless of the power setting of the trial lens system.

16. Apparatus as in claim 15 wherein said displaying means comprises a projector for projecting images of the test symbols onto a screen, and wherein said symbol size varying means comprises a pair of lenses coaxially positioned in the pathway of the projected symbol images, one lens of which is movable with respect to the other lens, under control of the data processing system, to vary the size of the symbols projected onto the screen.

17. Apparatus as in claim 10 wherein said displaying means comprises means for displaying a test symbol alternately at first and second spaced locations on the screen, and wherein said trial lens system includes means operable under control of the data processing system for providing a first power setting when the symbols are displayed at the first location and for providing a second power setting when the symbols are displayed at the second location.

18. Apparatus as in claim 17 wherein said manual response device is operable by the subject to identify to the data processing system one of two power settings preferred by the subject for viewing the test symbols.

19. Apparatus as in claim 10 wherein said displaying means comprises means for displaying a test symbol simultaneously at first and second spaced locations on the screen, wherein said apparatus further includes means for determining when the subjects direction of gaze shifts from the first location to the second location and vice versa, and wherein said control means is operable under control of the data processing system for changing the power setting of the trial lens system from a first power to a second power when the direction of gaze shifts from the first location to the second location and from the second power to the first power when the direction of gaze shifts from the second location to the first location.

20. Apparatus as in claim 19 wherein said manual response device is operable by the subject to identify to the data processing system one of two power settings preferred by the subject for viewing the test symbol.

21. Apparatus as in claim 18 further including timing means for supplying the data processing system with a signal indication of the time elapsed from initial display of a test symbol until either (a) the subject operates the manual response device, or (b) the data processing system applies a reset signal to the timing means, whichever occurs first.

22. Apparatus as in claim 20 further including timing means for supplying the data processing system with a signal indication of the time elapsed from initial display of a test symbol until either (a) the subject operates the manual response device, or (b) the data processing system applies a reset signal to the timing means, whichever occurs first.

23. Apparatus as in claim 10 wherein said trial lens system comprises first and second cylindrical lenses positioned one in front of the other in the pathway of the direction of the gaze of the subject so that the cylinder axes of the lenses are substantially perpendicular to the direction of gaze, each of said lenses being selectively rotatable, under control of the data processing system, about an axis coincident with the direction of gaze.

24. Apparatus for automatically measuring refractive error of the eye of a subject comprising:
a programmed data processing system,
display means operable under control of the data processing system for displaying test symbols,
a trial lens system through which the subject views the displayed symbols, said trial lens system operable under control of the data processing system to present various power settings to the subject,
response means enabling the subject to apply signals to the data processing system in response to viewing the displayed symbols,
objective means for objectively determining under control of the data processing system the visual acuity of the subject for any discrete power setting of the trial lens system,
said data processing system being programmed to determine the visual acuity of the subject a plurality of times as the refractive error is being measured in response to one of the objective refraction means and the response means, and cause the trial lens system to vary the power setting thereof based upon the measurements of visual acuity and signals received from the response means until the refractive error of the subject is determined, and
display means for indicating the refractive error of the subject.

25. Apparatus as in claim 24 wherein said display means comprises a screen, and
means for projecting light images of the test symbols onto the screen.

26. Apparatus as in claim 25 wherein said projecting means includes means operable under control of the data processing system for rotating the light images projected onto the screen.

27. Apparatus as in claim 26 wherein said rotating means includes
a dove prism positioned in the pathway of the light images projected onto the screen, and
means operable under control of the data processing system for rotating said dove prism about an axis coincident with said pathway to thereby cause the projected light images to rotate.

28. Apparatus as in claim 25 wherein said projecting means includes means operable under control of the data processing system for causing the light images to be projected alternately at first and second spaced locations on the screen, and wherein said trial lens system includes means operable under control of the data processing system for presenting a first power setting to the subject when the light images are projected at the first location and for presenting a second power setting when the light images are projected at the second location.

29. Apparatus as in claim 25 wherein said projecting means includes means operable under control of the data processing system for causing the light images to be projected simultaneously at first and second spaced location on the screen, wherein said apparatus further includes means for determining when the subject's direction of gaze shifts from the first location to the second location and vice versa, and wherein said trial lens system includes means operable under control of the data processing system for changing the power setting of the trial lens system from a first power to a second power when the direction of gaze shifts from the first location to the second location and from the second power to the first power when the direction of gaze shifts from the second location to the first location.

30. Apparatus as in claim 29 wherein said causing means comprises a light beam splitting prism positioned in the pathway of the light images projected onto the screen to thereby cause the light images to be projected simultaneously at said first and second locations.

31. Apparatus as in claim 25 wherein said projecting means includes means operable under control of the data processing system for varying the size of the light images projected onto the screen so that the apparent size of the symbols when viewed by the subject through the trial lens system remains constant even though the power setting of the trial lens system is changed.

32. Apparatus as in claim 31 wherein said light image size varying means comprises a pair of lenses coaxially positioned in the pathway of the light images projected onto the screen, one lens of which is movable, under control of the data processing system, with respect to the other lens.

33. Apparatus as in claim 24 wherein said data processing system is programmed to cause the symbol displaying means to vary the size of the displayed symbols in response to the signals received from the signal enabling means.

34. Apparatus as in claim 33 wherein said symbol displaying means comprises:
a screen,
means for projecting a beam of light onto the screen, and
a plurality of transparencies, each containing a different size symbol image and each selectively movable to a position in the pathway of the light beam so that the symbol image contained thereon is projected onto the screen.

35. Apparatus as in claim 24 wherein said trial lens system comprises:
first and second lenses coaxially positioned apart, and
means for varying the effective distance between the first and second lenses in a continuous fashion to thereby vary the power of the trial lens system.

36. Apparatus as in claim 35 wherein said varying means comprises:
first reflective means positioned between said first and second lenses for reflecting in a direction lateral to the axis of the first and second lenses light traveling along the axis of the lenses from the displayed symbols through said first lens,
second reflective means positioned laterally of the axis of the lenses and movable, under control of the data processing system, toward or away from the axis, for reflecting light received from said first reflective means back toward the axis of the lenses, and
third reflective means positioned between the first reflective means and the second lens for reflecting light from the second reflective means toward the second lens.

37. Apparatus as in claim 35 wherein said trial lens system further comprises turret means comprising a plurality of lenses, including said first lens, spaced about the periphery thereof, said turret means being rotatable, under control of the data processing system, to selectively position any one of said plurality of lenses coaxially with said second lens.

38. Apparatus as in claim 35 wherein said trial lens system further comprises a pair of cylindrical lenses positioned one in front of the other on the axis of the first and second lenses so that the cylinder axes of the cylindrical lenses are substantially perpendicular to the axis of the first and second lenses, each of said cylindrical lenses being selectively rotatable, under control of the data processing system, about the axis of the first and second lenses.

39. Apparatus as in claim 24 wherein the response means is manually operable by the subject to identify to the data processing system preferred power settings of the trial lens system from among a plurality of settings presented to the subject.

40. Apparatus as in claim 39 further including timing means for supplying the data processing system with a signal indication of the time elapsed from initial display of the test symbol until either (a) the subject operates the manual response device, or (b) the data processing system applies a reset signal to the timing means, whichever occurs first.

41. Apparatus as in claim 24 wherein the response means comprises a visually-evoked-response monitor for detecting the electrical activity in the occipital lobe of the brain of the subject and for signalling the data processing system accordingly.

42. Apparatus as in claim 24 wherein the objective means comprises means for displaying moving bars to the subject, and
means for monitoring, under control of the data processing system, the direction of gaze of the subject for determining if the subject's eyes exhibit a reflex following movement with the moving bars.

43. Apparatus as in claim 42 wherein the moving bars displaying means comprises a cathode ray tube.

44. Apparatus as in claim 24 further comprising an audio response system containing recorded messages which, under control of the data processing system, may be selectively reproduced to communicate the messages to the subject.

45. In an automatic process for subjectively determining the refractive error of a subject wherein the power of lenses presented to the subject is controlled by a data processing system in response to responses derived from the subject choosing between choices of images presented to the subject until an optimum lens power is determined and thereafter providing a readout of a lense prescription which provides refractive correction for the subject, the improvement comprising the steps of:
a. subjectively determining under control of the data processing system the visual acuity of the subject when viewing displayed test symbols, through a trial lens system set at a selected power, b. displaying under control of the data processing system alternately dark and light bars for viewing by the subject through the trial lens system, the bar width corresponding to some fraction of the visual acuity determined in the step (a), c. monitoring under control of the data processing system the direction of gaze of the subject to determine if the subject's eye exhibits a reflex following movement with the moving bars, d. if the subject's eye exhibits a reflex following movement, determining under control of the data processing system the visual acuity of the subject with the trial lens system set at the selected power using the optokinetic nystagmus test, and e. if the subject's eye does not exhibit a reflex following movement, setting a flag indicating that no reflex following movement was exhibited.

46. A process as in claim 45 wherein step (a) includes the steps of:

f. displaying under control of the data processing system a series of test symbols of predetermined size for viewing by the subject through the trial lens system set at a selected power, g. determining, for each symbol displayed, whether the subject can correctly identify the symbol, h. displaying under control of the data processing system a series of test symbols of a size smaller than the size of the symbols previously displayed if more than a certain percentage of the symbols previously displayed were correctly identified, and recording the visual acuity corresponding to the symbol size of the symbols previously displayed, i. displaying under control of the data processing system a series of test symbols of a size larger than the size of the symbols previously displayed if less than a certain percentage of the symbols previously displayed were correctly identified, j. performing step (g), and k. repeating steps (h) through (j) until either (1) less than a certain percentage of a series of displayed symbols are correctly identified following a decrease in the size of the symbols displayed, or (2) less than a certain percentage of a series of displayed symbols are correctly identified and the size of the symbols displayed is a certain maximum size.

47. A process as in claim 46 wherein step (d) includes the steps of:

l. displaying under control of the data processing system alternately dark and light bars for viewing by the subject through the trial lens system set at the selected power, the bar width corresponding to the most recently recorded visual acuity of the subject, m. monitoring under control of the data processing system the direction of gaze of the subject to determine if the subject's eye exhibits a reflex following movement with the moving bars, n. displaying under control of the data processing system alternately dark and light bars of a width less than the width of the moving bars previously displayed if the subject's eye exhibited a reflex following movement with the previously displayed moving bars, and recording the visual acuity corresponding to the bar width of the moving bars previously displayed, o. displaying under control of the data processing system alternately dark and light bars of a width greater than the width of the moving bars previously displayed if the subject's eye did not exhibit a reflex following movement with the previously displayed moving bars, p. performing step (m), and q. repeating steps (n) through (p) until either (1) no reflex following movement is exhibited by the subject's eye with displayed moving bars following a decrease in the width of the displayed moving bars, or (2) no reflex following movement is exhibited by the subject's eye with displayed moving bars and the width of the displayed moving bars is a certain maximum width.

48. A process as in claim 47 further including the steps of:

r. presenting test stimuli for viewing by the subject through the trial lens set alternately at the selected power + D and the selected power − D where D has a first value if the most recently recorded visual acuity is greater than a predetermined threshold value and where has a second value greater than said first value if the most recently recorded visual acuity is less than the threshold value, and s. determining under control of the data processing system whether one of the selected power + D or selected power settings of the trial lens system − D is a preferred for viewing of the test stimuli by the subject.

* * * * *